(12) United States Patent
Wang et al.

(10) Patent No.: US 10,457,721 B2
(45) Date of Patent: Oct. 29, 2019

(54) ANTI-OSPA ANTIBODIES AND METHODS OF USE

(71) Applicant: University of Massachusetts, Boston, MA (US)

(72) Inventors: Yang Wang, Natick, MA (US); William D. Thomas, Jr., Dedham, MA (US); Naomi K. Boatright, North Quincy, MA (US); Mark S. J. Klempner, Wayland, MA (US)

(73) Assignee: University of Massachusetts, Boston, MA (US)

( * ) Notice: Subject to any disclaimer, the term of this patent is extended or adjusted under 35 U.S.C. 154(b) by 168 days.

(21) Appl. No.: 15/501,469

(22) PCT Filed: Aug. 7, 2015

(86) PCT No.: PCT/US2015/044307
§ 371 (c)(1),
(2) Date: Feb. 3, 2017

(87) PCT Pub. No.: WO2016/025331
PCT Pub. Date: Feb. 18, 2016

(65) Prior Publication Data
US 2017/0226193 A1 Aug. 10, 2017

Related U.S. Application Data

(60) Provisional application No. 62/162,279, filed on May 15, 2015, provisional application No. 62/035,960, filed on Aug. 11, 2014.

(51) Int. Cl.
| | |
|---|---|
| *A61K 39/12* | (2006.01) |
| *C07K 14/005* | (2006.01) |
| *C07K 16/08* | (2006.01) |
| *G01N 33/569* | (2006.01) |
| *C07K 16/12* | (2006.01) |
| *C12P 21/00* | (2006.01) |
| *A61K 39/00* | (2006.01) |

(52) U.S. Cl.
CPC ........ *C07K 16/1207* (2013.01); *C12P 21/005* (2013.01); *G01N 33/56911* (2013.01); *A61K 2039/505* (2013.01); *C07K 2317/21* (2013.01); *C07K 2317/52* (2013.01); *C07K 2317/565* (2013.01); *C07K 2317/72* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| | | |
|---|---|---|
| 2011/0262475 A1 | 10/2011 | Earnhart et al. |
| 2012/0020973 A1 | 1/2012 | Crowe et al. |
| 2013/0273572 A1 | 10/2013 | Wagner |

OTHER PUBLICATIONS

De Silva et al. (Journal of Experimental Medicine, 1996, 183:271-275).*
Padlan (Advances in Protein Chemistry, 1996, 49:57-133).*
Berglund et al. (Protein Science, 2008, 17:606-613).*
Corada (Blood, 2001; 97:1679-84).*
(Kulkarni-Kale et al. Nucleic Acid Research, 2005, 33:W168-W171).*
Almagro & Fransson, Frontiers in Bioscience 2008; 13:1619-33.*
De Genst et al., Developmental and Comparative Immunology, 2006, 30:187-98.*
Ward et al. (Nature, 1989, 341:544-546).*
Barthelemy et al. (Journal of Biological Chemistry, 2008, 283:3639-3654).*
Choi et al., 2011, Molecular BioSystems, 2011, 7:3327-334.*
Griffiths et al. (The EMBO Journal, 1993, 12:725-734).*
Klimka et al., British Journal of Cancer, 2000, 83:252-260.*
Beiboer et al. (Journal of Molecular Biology, 2000, 296:833-849).*
Ding et al., "Structural identification of a key protective B-cell epitope in Lyme disease antigen OspA," J Mol Biol. 302(5):1153-64 (2000).
Jiang et al., "Purification of Borrelia burgdorferi outer surface protein A (OspA) and analysis of antibody binding domains," Clin Diagn Lab Immunol. 1(4):406-12 (1994).
Luft et al., "Approaches toward the directed design of a vaccine against Borrelia burgdorferi," J Infect Dis. 185 Suppl 1:S46-51 (2002).
Ma et al., "Molecular analysis of neutralizing epitopes on outer surface proteins A and B of Borrelia burgdorferi," Infect Immun. 63(6):2221-7 (1995).
Wang et al., "Discovery of OspA-specific human monoclonal antibodies reactive against a broad range or *borrelia* species for the prevention of lyme disease," IDWEEK, 2015 (Poster presentation) (1 page).
Extended European Search Report for European Patent Application No. 15831958.2, dated Dec. 6, 2017 (9 pages).
International Preliminary Report on Patentability for International Application No. PCT/US2015/044307, dated Jun. 27, 2016 (49 pages).
International Search Report and Written Opinion for International Application No. PCT/US2015/044307, dated Jan. 6, 2016 (13 pages).

* cited by examiner

*Primary Examiner* — Julie Wu
(74) *Attorney, Agent, or Firm* — Clark & Elbing LLP

(57) ABSTRACT

The invention provides anti-OspA antibodies and methods of using the same.

44 Claims, 7 Drawing Sheets

Specification includes a Sequence Listing.

Figure 1A

HuMab borreliacidal activity against *B. burgdorferi*

US 10,457,721 B2

ANTI-OSPA ANTIBODIES AND METHODS OF USE

BACKGROUND OF THE INVENTION

Human Lyme borreliosis (LB), commonly known as Lyme disease, is the most prevalent vector-borne infection in temperate climate zones around the world. Lyme disease is caused by bacterial spirochetes belonging to the genus *Borrelia*, and three pathogenic species of *Borrelia*, in particular, are associated with Lyme disease in humans: *Borrelia burgdorferi*, *Borrelia garinii*, and *Borrelia afzelii*. *Borrelia burgdorferi* causes of Lyme disease in North America, whereas *Borrelia garinii* and *Borrelia afzelii* are the causative agents in most European and Asian cases. *Borrelia* is mainly transmitted to humans by the bite of infected ticks belonging to a few species of the genus *Ixodes*, such as the blacklegged tick (or deer tick, *Ixodes scapularis*) that spreads the disease in the northeastern, mid-Atlantic, and north-central United States, and the western blacklegged tick (*Ixodes pacificus*) that spreads the disease on the Pacific Coast.

Lyme disease in humans is associated with inflammation and characterized by the skin lesion erythema migrans, as well as the potential development of neurologic, cardiac, and joint abnormalities. The Centers for Disease Control and Prevention now estimates based on preliminary statistics that the number of people newly diagnosed with Lyme disease each year in the United States alone is around 300,000. This is about ten times higher than the officially reported number of cases in the U.S., indicating that the disease is being vastly underreported. In Europe, approximately 85,000 Lynne disease cases occur annually.

The continued and marked prevalence of Lyme disease in the United States and throughout the world underscores the need for the development of an effective vaccine for the disease. Although clinical trials in the United States showed that Lyme disease could be prevented by vaccination with outer surface protein A (OspA), a major surface antigen encoded by all three *Borrelia* species associated with Lyme disease, the efficacy of the vaccine was limited to *Borrelia burgdorferi* due to antigenic heterogeneity of OspA across the three pathogenic *Borrelia* species. Currently, there exists no vaccine available in the United States for human Lyme disease caused by *Borrelia burgdorferi*, much less a vaccine that also protects against *Borrelia garinii* and/or *Borrelia afzelii*. Accordingly, there remains an unmet need in the field for the development of an effective Lyme disease vaccine, particularly a vaccine that would protect against Lyme disease caused by all three pathogenic *Borrelia* species.

SUMMARY OF THE INVENTION

The present invention relates to anti-outer surface protein A (OspA) antibodies and methods of their use.

In a first aspect, the invention features an isolated antibody that specifically binds to OspA, wherein the antibody binds to an epitope comprising amino acid residues 71-141 of OspA (SEQ ID NO: 1) (e.g., an epitope comprising amino acid residues 71-273), or an epitope comprising amino acid residues having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99 identity) to SEQ ID NO: 1. In some embodiments, the antibody comprises one, two, or three of the following complementarity determining regions (CDRs): (a) a CDR-H1 comprising the amino acid sequence of $GYX_1FX_2SYWIG$, wherein $X_1$ is S or K and $X_2$ is T or S (SEQ ID NO: 2); (b) a CDR-H2 comprising the amino acid sequence of $X_1IX_2PGDSDX_3RYSPSFQG$, wherein $X_1$ is F or I, $X_2$ is Y or F, and $X_3$ is T or K (SEQ ID NO: 3); and/or (c) a CDR-H3 comprising the amino acid sequence of ARGILRYFDWFLDY (SEQ ID NO: 4) or ARHITTHTYRGFFDF (SEQ ID NO: 5), or a combination of one or more of the above CDRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 2, 3, 4, and/or 5. In some embodiments, the antibody comprises one, two, or three of the following CDRs: (a) a CDR-L1 comprising the amino acid sequence of $RASQX_1ISSX_2X_3A$, wherein $X_1$ is G or D, $X_2$ is G or A, and $X_3$ is S or L (SEQ ID NO: 6); (b) a CDR-L2 comprising the amino acid sequence of DVSSLES (SEQ ID NO: 7); and/or (c) a CDR-L3 comprising the amino acid sequence of QQFNSYLLT (SEQ ID NO: 8) or QQFNGYPHRLT (SEQ ID NO: 9), or a combination of one or more of the above CDRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 6, 7, 8, and/or 9.

In some embodiments, the antibody comprises one, two, three, four, five, all six of the following CDRs: (a) a CDR-H1 comprising the amino acid sequence of $GYX_1FX_2SYWIG$, wherein $X_1$ is S or K and $X_2$ is T or S (SEQ ID NO: 2); (b) a CDR-H2 comprising the amino acid sequence of $X_1IX_2PGDSDX_3RYSPSFQG$, wherein $X_1$ is F or I, $X_2$ is Y or F, and $X_3$ is T or K (SEQ ID NO: 3); (c) a CDR-H3 comprising the amino acid sequence of ARGILRYFDWFLDY (SEQ ID NO: 4) or ARHITTHTYRGFFDF (SEQ ID NO: 5); (d) a CDR-L1 comprising the amino acid sequence of $RASQX_1ISSX_2X_3A$, wherein $X_1$ is G or D, $X_2$ is G or A, and $X_3$ is S or L (SEQ ID NO: 6); (e) a CDR-L2 comprising the amino acid sequence of DVSSLES (SEQ ID NO: 7); and/or (f) a CDR-L3 comprising the amino acid sequence of QQFNSYLLT (SEQ ID NO: 8) or QQFNGYPHRLT (SEQ ID NO: 9), or a combination of one or more of the above CDRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 2-9.

In one embodiment, the antibody one, two, three, four, five, all six of the following CDRs: (a) a CDR-H1 comprising the amino acid sequence of GYSFTSYWIG (SEQ ID NO: 10); (b) a CDR-H2 comprising the amino acid sequence of FIYPGDSDTRYSPSFQG (SEQ ID NO: 11); (c) a CDR-H3 comprising the amino acid sequence of ARGILRYFDWFLDY (SEQ ID NO: 4); (d) a CDR-L1 comprising the amino acid sequence of RASQGISSGSA (SEQ ID NO: 12); (e) a CDR-L2 comprising the amino acid sequence of DVSSLES (SEQ ID NO: 7); and/or (f) a CDR-L3 comprising the amino acid sequence of QQFNSYLLT (SEQ ID NO: 8), or a combination of one or more of the above CDRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 2-9. In some embodiments, the antibody comprises (a) a heavy chain variable domain (VH) sequence having at least 90% sequence identity (e.g., at least 91%, 92%, 93%, 94%, 95%, 96%, 97%, 98%, or 99% sequence identity) to, or the sequence of, SEQ ID NO: 13; (b) a light chain variable domain (VL) sequence having at least 90% sequence identity (e.g., at least 91%, 92%, 93%, 94%, 95%, 96%, 97%, 98%, or 99% sequence identity) to, or the sequence of, SEQ ID NO: 14; or (c) a VH sequence as in (a) and a VL sequence as in (b). For example, in some embodiments, the antibody comprises (a) a VH sequence comprising the amino acid sequence of SEQ ID NO: 13; (b) a VL sequence comprising the amino acid sequence of SEQ ID NO: 14; or (c) a VH sequence as in (a) and a VL sequence as in (b). In some embodiments, the antibody binds to an epitope comprising amino acid residues 71-105 of OspA (SEQ ID NO: 15) (e.g., an epitope comprising amino acid residues 71-273). In a particular embodiment, the antibody is anti-OspA antibody 221-7.

In another embodiment, the antibody one, two, three, four, five, all six of the following CDRs: (a) a CDR-H1 comprising the amino acid sequence of GYKFSSYWIG (SEQ ID NO: 16); (b) a CDR-H2 comprising the amino acid sequence of IIFPGDSDKRYSPSFQG (SEQ ID NO: 17); (c) a CDR-H3 comprising the amino acid sequence of ARHITTH-TYRGFFDF (SEQ ID NO: 5); (d) a CDR-L1 comprising the amino acid sequence of RASQDISSALA (SEQ ID NO: 18); (e) a CDR-L2 comprising the amino acid sequence of DVSSLES (SEQ ID NO: 7); and/or (f) a CDR-L3 comprising the amino acid sequence of QQFNGYPHRLT (SEQ ID NO: 9), or a combination of one or more of the above CDRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 5, 7, 9, and 16-18. In some embodiments, the antibody comprises (a) a VH sequence having at least 90% sequence identity (e.g., at least 91%, 92%, 93%, 94%, 95%, 96%, 97%, 98%, or 99% sequence identity) to, or the sequence of, SEQ ID NO: 19; (b) a VL sequence having at least 90% sequence identity (e.g., at least 91%, 92%, 93%, 94%, 95%, 96%, 97%, 98%, or 99% sequence identity) to, or the sequence of, SEQ ID NO: 20; or (c) a VH sequence as in (a) and a VL sequence as in (b). For example, in some embodiments, the antibody comprises (a) a VH sequence comprising the amino acid sequence of SEQ ID NO: 19; (b) a VL sequence comprising the amino acid sequence of SEQ ID NO: 20; or (c) a VH sequence as in (a) and a VL sequence as in (b). In some embodiments, the antibody binds to an epitope comprising amino acid residues 106-141 of OspA (SEQ ID NO: 21) (e.g., an epitope comprising amino acid residues 106-273). In a particular embodiment, the antibody is anti-OspA antibody 857-2.

In any of the above embodiments of the first aspect, the antibody may bind to three or more *Borrelia* species. In some embodiments, the three or more *Borrelia* species comprises *Borrelia burgdorferi, Borrelia afzelii*, and *Borrelia garinii*. In some embodiments, the antibody binds to OspA of *Borrelia burgdorferi, Borrelia afzelii*, and *Borrelia garinii* with a $K_D$ of at least about 50 nM or lower. In some embodiments, the antibody exhibits borreliacidal activity against *Borrelia* species comprising *Borrelia burgdorferi, Borrelia afzelii*, and *Borrelia garinii* in a borreliacidal assay. In some embodiments, the antibody is capable of killing *Borrelia burgdorferi, Borrelia afzelii*, and/or *Borrelia garinii* in a *Borrelia* vector (e.g., a tick of the genus *Ixodes*).

In a second aspect, the invention features an isolated antibody that specifically binds to outer surface protein A (OspA), wherein the antibody binds to an epitope comprising amino acid residues 178-273 of OspA (SEQ ID NO: 22), or an epitope comprising amino acid residues having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99 identity) to SEQ ID NO: 22. In some embodiments, the antibody comprises the following one, two, or three CDRs: (a) a CDR-H1 comprising the amino acid sequence of GYIFATYWIG (SEQ ID NO: 23); (b) a CDR-H2 comprising the amino acid sequence of IIYPNDSDTRYSPSFQG (SEQ ID NO: 24); and/or (c) a CDR-H3 comprising the amino acid sequence of ARTRWYFDL (SEQ ID NO: 25), or a combination of one or more of the above CDRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 23-25. In some embodiments, the antibody comprises the following one, two, or three CDRs: (a) a CDR-L1 comprising the amino acid sequence of RASQSVSSSYLA (SEQ ID NO: 26); (b) a CDR-L2 comprising the amino acid sequence of GASSRAT (SEQ ID NO: 27); and/or (c) a CDR-L3 comprising the amino acid sequence of QQYGSSPLT (SEQ ID NO: 28), or a combination of one or more of the above CDRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 26-28.

In some embodiments, the antibody one, two, three, four, five, all six of the following CDRs: (a) a CDR-H1 comprising the amino acid sequence of GYIFATYWIG (SEQ ID NO: 23); (b) a CDR-H2 comprising the amino acid sequence of IIYPNDSDTRYSPSFQG (SEQ ID NO: 24); (c) a CDR-H3 comprising the amino acid sequence of ARTRWYFDL (SEQ ID NO: 25); (d) a CDR-L1 comprising the amino acid sequence of RASQSVSSSYLA (SEQ ID NO: 26); (e) a CDR-L2 comprising the amino acid sequence of GASSRAT (SEQ ID NO: 27); and/or (f) a CDR-L3 comprising the amino acid sequence of QQYGSSPLT (SEQ ID NO: 28), or a combination of one or more of the above CDRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 23-28. In some embodiments, the antibody comprises (a) a heavy chain variable domain (VH) sequence having at least 90% sequence identity (e.g., at least 91%, 92%, 93%, 94%, 95%, 96%, 97%, 98%, or 99% sequence identity) to, or the sequence of, SEQ ID NO: 29; (b) a light chain variable domain (VL) sequence having at least 90% sequence identity (e.g., at least 91%, 92%, 93%, 94%, 95%, 96%, 97%, 98%, or 99% sequence identity) to, or the sequence of, SEQ ID NO: 30; or (c) a VH sequence as in (a) and a VL sequence as in (b). In some embodiments, the antibody comprises (a) a VH sequence comprising the amino acid sequence of SEQ ID NO: 29; (b) a VL sequence comprising the amino acid sequence of SEQ ID NO: 30; or (c) a VH sequence as in (a) and a VL sequence as in (b). In a particular embodiment, the antibody is anti-OspA antibody 319-44.

In any of the above embodiments of the second aspect, the antibody may bind to two or more *Borrelia* species. In some embodiments, the two or more *Borrelia* species comprises *Borrelia burgdorferi* and *Borrelia afzelii*. In some embodiments, the antibody binds to OspA of *Borrelia burgdorferi* and *Borrelia afzelii* with a $K_D$ of at least about 1.2 µM or lower. In some embodiments, the antibody binds to OspA of *Borrelia burgdorferi* with a $K_D$ of at least about 350 nM or lower. In some embodiments, the antibody exhibits borreliacidal activity against *Borrelia* species comprising *Borrelia burgdorferi* and *Borrelia afzelii* in a borreliacidal assay. In some embodiments, the antibody is capable of killing *Borrelia burgdorferi* and *Borrelia afzelii* in a *Borrelia* vector (e.g., a tick of the genus *Ixodes*).

In a third aspect, the invention features an isolated antibody that specifically binds to outer surface protein A (OspA), wherein the antibody binds to an epitope comprising amino acid residues 142-177 of OspA (SEQ ID NO: 31) (e.g., an epitope comprising amino acid residues 142-273). In some embodiments, the antibody comprises one, two, or three of the following CDRs: (a) a CDR-H1 comprising the amino acid sequence of GFTFRNYWMD (SEQ ID NO: 32); (b) a CDR-H2 comprising the amino acid sequence of NIKQDGSVKYYVDSVEG (SEQ ID NO: 33); and/or (c) a CDR-H3 comprising the amino acid sequence of ARDGYS-GYDSVGFDI (SEQ ID NO: 34), or a combination of one or more of the above CDRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 32-34. In some embodiments, the antibody comprises one, two, or three of the following CDRs: (a) a CDR-L1 comprising the amino acid sequence of RASQSVSSSYLA (SEQ ID NO: 35); (b) a CDR-L2 comprising the amino acid sequence of DTSSRAT (SEQ ID NO: 36); and/or (c) a CDR-L3 comprising the amino acid sequence of QQYGSSPYT (SEQ ID NO: 37), or a combination of one or more of the above CDRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 35-37.

In some embodiments, the antibody comprises one, two, three, four, five, all six of the following CDRs: (a) a CDR-H1 comprising the amino acid sequence of GFTFRNYWMD (SEQ ID NO: 32); (b) a CDR-H2 comprising the amino acid sequence of NIKQDGSVKYYVDSVEG (SEQ ID NO: 33); (c) a CDR-H3 comprising the amino acid sequence of ARDGYSGYDSVGFDI (SEQ ID NO: 34); (d) a CDR-L1 comprising the amino acid sequence of RASQS-VSSSYLA (SEQ ID NO: 35); (e) a CDR-L2 comprising the amino acid sequence of DTSSRAT (SEQ ID NO: 36); and/or (f) a CDR-L3 comprising the amino acid sequence of QQYGSSPYT (SEQ ID NO: 37), or a combination of one or more of the above CDRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 32-37. In some embodiments, the antibody comprises (a) a heavy chain variable domain (VH) sequence having at least 90% sequence identity (e.g., at least 91%, 92%, 93%, 94%, 95%, 96%, 97%, 98%, or 99% sequence identity) to, or the sequence of, SEQ ID NO: 38; (b) a light chain variable domain (VL) sequence having at least 90% sequence identity (e.g., at least 91%, 92%, 93%, 94%, 95%, 96%, 97%, 98%, or 99% sequence identity) to, or the sequence of, SEQ ID NO: 39; or (c) a VH sequence as in (a) and a VL sequence as in (b). In some embodiments, the antibody comprises (a) a VH sequence comprising the amino acid sequence of SEQ ID NO: 38; (b) a VL sequence comprising the amino acid sequence of SEQ ID NO: 39; or (c) a VH sequence as in (a) and a VL sequence as in (b). In a particular embodiment, the antibody is anti-OspA antibody 212-55.

In any of the above embodiments of the third aspect, the antibody may bind to one or more *Borrelia* species. In some embodiments, the one or more *Borrelia* species comprises *Borrelia burgdorferi*. In some embodiments, the antibody binds to OspA of *Borrelia burgdorferi* with a $K_D$ of at least about 50 nM or lower. In some embodiments, the antibody binds to OspA of *Borrelia burgdorferi* with a $K_D$ of at least about 25 nM or lower. In some embodiments, the antibody exhibits borreliacidal activity against *Borrelia* species comprising *Borrelia burgdorferi* in a borreliacidal assay. In some embodiments, the antibody is capable of killing *Borrelia burgdorferi* in a *Borrelia* vector (e.g., a tick of the genus *Ixodes*).

In any of the above embodiments of the first, second, and third aspects, the antibody may be monoclonal, human, humanized, or chimeric. In some embodiments, the antibody is an antibody fragment that binds OspA. In some embodiments, the antibody fragment is selected from the group consisting of Fab, Fab'-SH, Fv, scFv, and (Fab')$_2$ fragments. In some embodiments, the antibody is a full-length antibody. In some embodiments, antibody is an IgG antibody (e.g., an IgG1 antibody). In some embodiments, the half-life of the antibody is ≥3 days (e.g., ≥1 week, e.g., ≥2 weeks, e.g., ≥1 month, e.g., ≥2 months, e.g., ≥3 months, e.g., ≥4 months, e.g., ≥5 months, e.g., ≥6 months).

In a fourth aspect, the invention features a pharmaceutical composition comprising an antibody of the first, second, or third aspect. In some embodiments, the invention features a pharmaceutical composition comprising two or more antibodies of the first, second, or third aspect, optionally wherein the two or more antibodies bind to different epitopes of OspA. In some embodiments, the pharmaceutical composition further comprises a pharmaceutically acceptable carrier, excipient, or diluent. In some embodiments, the pharmaceutical composition is formulated for treating a disorder associated with a *Borrelia* infection in a subject. In some embodiments, the disorder associated with a *Borrelia* infection is Lyme borreliosis (Lyme disease).

In a fifth aspect, the invention features an isolated nucleic acid encoding one or more antibodies (e.g., 1, 2, or 3 or more antibodies) of the first, second, and/or third aspects.

In a sixth aspect, the invention features a vector comprising a nucleic acid of the fifth aspect.

In a seventh aspect, the invention features a host cell comprising a vector of the sixth aspect. In some embodiments, the host cell is a mammalian cell (e.g., a Chinese hamster ovary (CHO) cell). In other embodiments, the host cell is a prokaryotic cell (e.g., *E. coli*).

In an eighth aspect, the invention features a method of producing an antibody of the first, second, and/or third aspect, the method comprising culturing a host cell of the seventh aspect in a culture medium. In some embodiments, the method further comprises recovering the antibody from the host cell or the culture medium.

In a ninth aspect, the invention features a method of treating a subject having a disorder associated with a *Borrelia* infection comprising administering a therapeutically effective amount of an antibody of the first, second, and/or third aspect or a pharmaceutical composition of the fourth aspect, thereby treating the subject.

In a tenth aspect, the invention features a method of treating a subject at risk of developing a disorder associated with a *Borrelia* infection comprising administering a therapeutically effective amount of an antibody of the first, second, and/or third aspect or a pharmaceutical composition of the fourth aspect, thereby treating the subject.

In certain embodiments of the ninth or tenth aspect, the antibody is administered to the subject in a dosage of about 0.01 mg/kg to about 10 mg/kg (e.g., about 0.1 mg/kg to about 10 mg/kg, e.g., about 1 mg/kg to about 10 mg/kg). In some embodiments, the antibody is administered intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, in cremes, or in lipid compositions. In some embodiments, the disorder associated with a *Borrelia* infection is Lyme borreliosis (Lyme disease). In some embodiments, the subject is administered at least one dose of the antibody or the pharmaceutical composition. In some embodiments, the subject is administered at least two doses of the antibody or the pharmaceutical composition. In some embodiments, the subject is at risk of developing the disorder associated with a *Borrelia* infection following being bitten by a *Borrelia* vector (e.g., a tick of the genus *Ixodes*).

In an eleventh aspect, the invention features a method of testing a *Borrelia* vector (e.g., a tick of the genus *Ixodes*) for the presence of *Borrelia*, the method comprising contacting a sample from the *Borrelia* vector with an antibody of the first, second, and/or third aspect and determining if binding occurs, wherein binding is indicative of the presence of a *Borrelia*.

In a twelfth aspect, the invention features a method of decreasing *Borrelia* load in a *Borrelia* vector (e.g., a tick of the genus *Ixodes*), the method comprising providing an antibody of the first, second, and/or third aspect of the invention to the *Borrelia* vector.

In a thirteenth aspect, the invention features a method of detecting a *Borrelia* infection in a subject comprising contacting a body fluid of the subject with an antibody of the first, second, and/or third aspect of the invention and determining if binding occurs, wherein binding is indicative of the presence of a *Borrelia* infection.

In a final aspect, the invention features a method of treating a subject having a disorder associated with a *Borrelia* infection comprising administering a therapeutically effective amount of a monoclonal antibody that specifically binds to OspA or a pharmaceutical composition thereof, thereby treating the subject.

Other features and advantages of the invention will be apparent from the following description of the preferred embodiments thereof, and from the claims.

BRIEF DESCRIPTION OF THE DRAWINGS

FIG. 1A is a graph showing the borreliacidal activities of anti-OspA human monoclonal antibodies (HuMabs) antibodies 221-7, 857-2, 319-44, and 212-55 against the *Borrelia* species *B. burgdorferi* B31, as compared to that of anti-OspA antibody LA-2 and an irrelevant HuMab control (CDA1).

DETAILED DESCRIPTION OF EMBODIMENTS OF THE INVENTION

I. Definitions

Figure 1B:
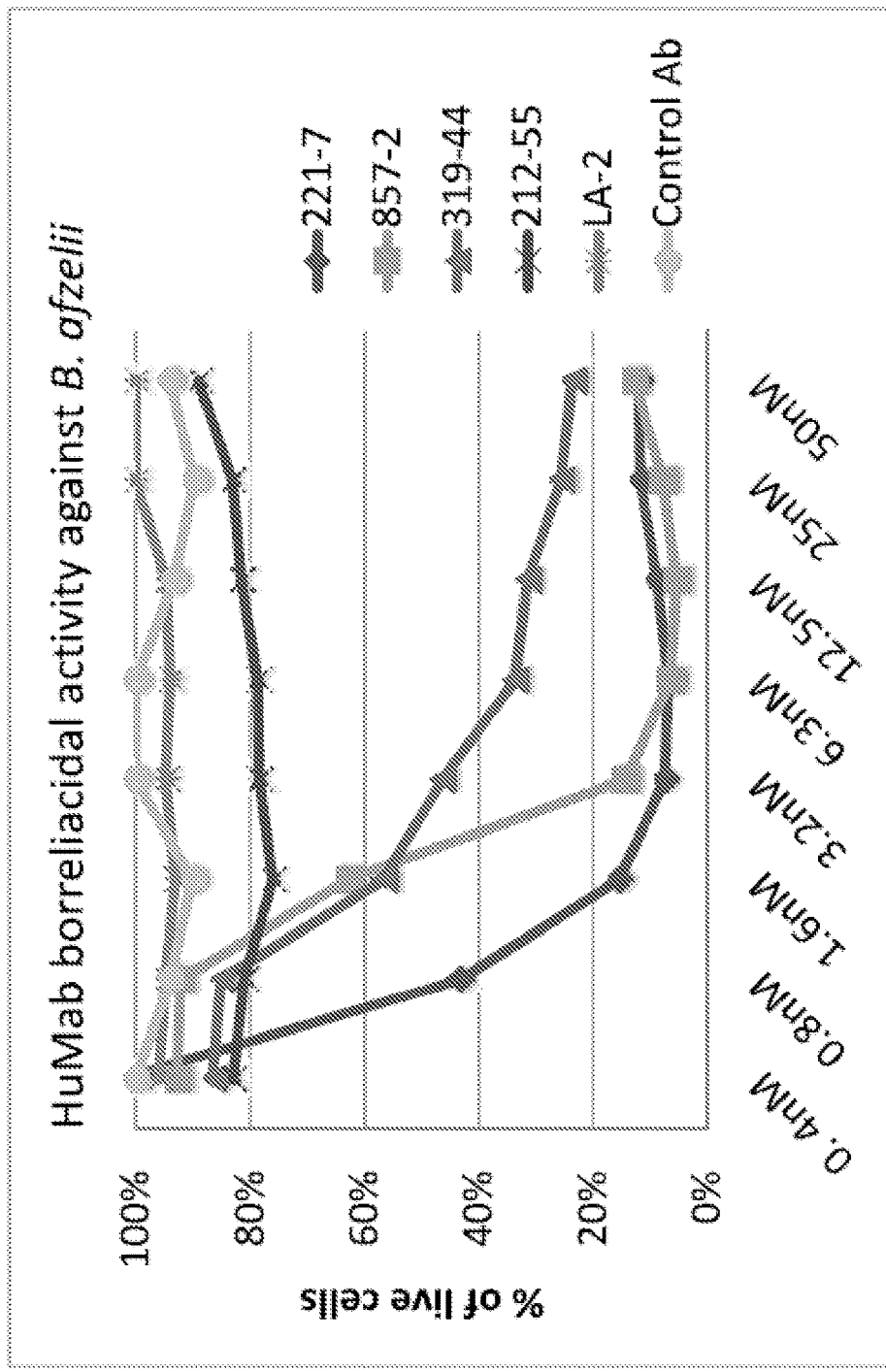
FIG. 1B is a graph showing the borreliacidal activities of anti-OspA HuMabs antibodies 221-7, 857-2, 319-44, and 212-55 against the *Borrelia* species *B. afzelii* BO23, as compared to that of antibodies LA-2 and CDA1.

The terms "anti-OspA antibody," "an antibody that binds to OspA," and "an antibody that specifically binds to OspA" refer to an antibody that is capable of binding OspA with sufficient affinity such that the antibody is useful as a preventative, diagnostic, and/or therapeutic agent in targeting OspA. In one embodiment, the extent of binding of an anti-OspA antibody to an unrelated, non-OspA protein is less than about 10% of the binding of the antibody to OspA as measured, e.g., by a radioimmunoassay (RIA). In certain embodiments, an antibody that binds to OspA has a dissociation constant ($K_D$) of ≤1 µM, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g., from $10^{-9}$M to $10^{-13}$ M). In certain embodiments, an anti-OspA antibody binds to an epitope of OspA that is conserved among OspA from different *Borrelia* species.

The term "*Borrelia*" refers to a genus of bacteria of the spirochete phylum and includes, for example, pathogenic, minimally pathogenic, and non-pathogenic *Borrelia* species. Pathogenic species of *Borrelia* include, for example, *B. burgdorferi* sensu stricto (also referred to as *B. burgdorferi* or B.b.s.s.), *B. afzelii*, and *B. garinii* (see, e.g., Baranton, G., et al., *Int. J. Syst. Bacteriol.* 42:378-383 (1992)). Non-pathogenic or minimally pathogenic species of *Borrelia* include, for example, *Borrelia andersonii, Borrelia bissettii, Borrelia valaisiana, Borrelia lusitaniae, Borrelia spielmani, Borrelia japonica, Borrelia tanukii, Borrelia turdae,* and *Borrelia sinica.*

The term "*Borrelia* vector" refers to an agent (a person, animal, microorganism, etc.) that carries and is capable of transmitting, either actively or passively, one or more species of *Borrelia* to another living organism, such as a human. The most common *Borrelia* vector for Lyme disease, for example, is a tick of the genus *Ixodes,* which can carry the *Borrelia* in its midgut. The most common *Borrelia* vector for relapsing fever, for example, is the human body louse, *Pediculus humanus humanus,* which can also carry the *Borrelia* (e.g., *Borrelia recurrentis*) in its gut.

The term "outer surface protein A," "major outer surface protein A," or "OspA" as used herein refers to the approximately 31-kDa basic lipoprotein encoded by the ospA gene of *Borrelia* or recombinant forms, truncated forms, mutant forms (e.g., OspA having insertion, deletion, and/or substitution mutation(s); tagged OspA; labeled OspA), and fragment or partial forms thereof. In some embodiments, OspA refers to "full-length," unprocessed OspA of *Borrelia burgdorferi* having the 273-amino acid sequence of Genbank accession number NP_045688 (SEQ ID NO: 40). In some embodiments, OspA refers to a truncated form of OspA without a leader sequence (the N-terminal 17 amino acids of full-length OspA) that is unlipidated and has the amino acid sequence of SEQ ID NO: 43 (OspA 18-273). In some instances, lipidation is known to impair both the solubility of the wild-type OspA protein as well as the expression and processing of the wild-type OspA protein within a host bacterium, such as *E. coli*. The term OspA, as noted above, also includes mutant forms of OspA.

The term "antibody" as used herein in the broadest sense encompasses various antibody structures, including but not limited to monoclonal antibodies, polyclonal antibodies, multispecific antibodies (e.g., bispecific antibodies), and antibody fragments so long as they exhibit the desired antigen-binding activity. An "antibody" can refer, for example, to a glycoprotein comprising at least two heavy chains (HCs) and two light chains (LCs) inter-connected by disulfide bonds, or an antigen binding portion thereof. Each heavy chain is comprised of a heavy chain variable region (VH) and a heavy chain constant region (CH). The heavy chain constant region may be comprised of three domains, CH1, CH2, and/or CH3. Each light chain is comprised of a light chain variable region (VL) and a light chain constant region (CL). The VH and VL regions can be further subdivided into regions of hypervariability, termed "complementarity determining regions" (CDRs), interspersed with regions that are more conserved, termed "framework regions" (FRs). Each VH and VL may be composed, for example, of three CDRs and four FRs, arranged from amino-terminus to carboxyl-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The terms "full-length antibody," "intact antibody," and "whole antibody" are used herein interchangeably to refer to an antibody having a structure substantially similar to a native antibody structure or having heavy chains that contain an Fc region as defined herein.

The term "human antibody" includes antibodies having variable and constant regions (if present) of human germline immunoglobulin sequences. Human antibodies of the invention can include amino acid residues not encoded by human germline immunoglobulin sequences (e.g., mutations introduced by random or site-specific mutagenesis in vitro or by somatic mutation in vivo) (see, Lonberg, N. et al. (1994) Nature 368(6474): 856-859); Lonberg, N. (1994) Handbook of Experimental Pharmacology 113:49-101; Lonberg, N. and Huszar, D. (1995) Intern. Rev. Immunol. Vol. 13: 65-93, and Harding, F. and Lonberg, N. (1995) Ann. N.Y. Acad. Sci 764:536-546). However, the term "human antibody" does not include antibodies in which CDR sequences derived from the germline of another mammalian species, such as a mouse, have been grafted onto human framework sequences (i.e., humanized antibodies).

The term "monoclonal antibody," as used herein, refers to an antibody which displays a single binding specificity and affinity for a particular epitope. Accordingly, the term "human monoclonal antibody," or "HuMab," refers to an antibody which displays a single binding specificity and which has variable and constant regions derived from human germline immunoglobulin sequences. In one embodiment, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

An "antibody fragment" refers to a molecule other than an intact antibody that comprises a portion of an intact antibody that specifically binds to the antigen (e.g., *Borrelia* or an OspA protein thereof) to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments. These antibody fragments are obtained using conventional techniques, and the fragments are screened for utility in the same manner as are intact antibodies. Antibody fragments can be produced by recombinant DNA techniques, or by enzymatic or chemical cleavage of intact immunoglobulins.

The term "about" as used herein refers to the usual error range for the respective value readily known to the skilled person in this technical field. Reference to "about" a value or parameter herein includes (and describes) embodiments that are directed to that value or parameter per se.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Specific illustrative and exemplary embodiments for measuring binding affinity are described below.

The term "$K_D$," as used herein, is intended to refer to the dissociation equilibrium constant of a particular antibody-antigen interaction. Typically, the antibodies of the invention bind to OspA of at least one *Borrelia* species with a dissociation equilibrium constant ($K_D$) of less than about $10^{-6}$ M, such as less than approximately $10^{-7}$ M, $10^{-8}$ M, $10^{-9}$ M, or $10^{-10}$ M or even lower when determined by surface plasmon resonance (SPR) technology in a BIA- CORE 3000 instrument using recombinant OspA of *B. burgdorferi, B. garinii,* or *B. afzelii* as the analyte and the antibody as the ligand.

As used herein, the term "borreliacidal activity" is used to refer to the ability of an antibody of the invention to kill one or more *Borrelia* species or impair the pathogenicity one or more *Borrelia* species.

A "disorder" is any condition that would benefit from treatment including, but not limited to, chronic and acute disorders or diseases including those pathological conditions which predispose the mammal to the disorder in question.

As used herein, the term "disorder associated with a *Borrelia* infection" refers to any disease, the onset, progression, or the persistence of the symptoms of which requires the participation of a *Borrelia* spirochete. An exemplary disorder associated with a *Borrelia* infection is, for example, Lyme borreliosis (LB; also referred to as Lyme disease). Other disorders associated with a *Borrelia* infection include relapsing fever, for which the body louse (*Pediculus humanus humanus*) is a vector.

The term "EC50," as used herein, refers to the concentration of an antibody or an antigen-binding portion thereof, which induces a response, either in an in vivo or an in vitro assay, such as a borreliacidal activity assay described herein, which is 50% of the maximal response (i.e., halfway between the maximal response and the baseline).

The terms "effective amount," "effective dose," and "effective dosage" as used herein are defined as an amount sufficient to achieve, or at least partially achieve, the desired effect. The term "therapeutically effective dose" or "therapeutically effective amount" is defined as an amount sufficient to prevent, cure, or at least partially arrest, the disease (e.g., Lyme disease) and its complications in a patient already suffering from the disease or at risk of developing the disease. Amounts effective for this use will depend upon the severity of the disorder being treated and the general state of the patient's own immune system.

The term "epitope" or "antigenic determinant" refers to a site on an antigen to which an immunoglobulin or antibody specifically binds (e.g., OspA of *Borrelia*, such as, amino acids 71-141 of OspA (SEQ ID NO: 1)). Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include techniques in the art and those described herein, for example, x-ray crystallography and 2-dimensional nuclear magnetic resonance. See, for example, Epitope Mapping Protocols in Methods in Molecular Biology, Vol. 66, G. E. Morris, Ed. (1996). Epitopes can also be defined by point mutations in the target protein (e.g., OspA of *Borrelia*), which affect the binding of the antibody (e.g., monoclonal antibody).

The term "host cell," as used herein, is intended to refer to a cell into which an expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

An "isolated antibody" is one which has been identified and separated and/or recovered from a component of its natural environment and/or is substantially free of other antibodies having different antigenic specificities (e.g., an isolated antibody that specifically binds to OspA is substantially free of antibodies that specifically bind antigens other than OspA). Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie™ blue or, preferably, silver stain. Isolated antibody includes the antibody in situ within recombinant cells since at least one component of the antibody's natural environment will not be present. Similarly, isolated antibody includes the antibody in medium around recombinant cells. Ordinarily, however, isolated antibody will be prepared by at least one purification step.

The term "nucleic acid molecule," as used herein, is intended to include DNA molecules and RNA molecules. A nucleic acid molecule may be single-stranded or double-stranded, but preferably is double-stranded DNA.

The term "isolated nucleic acid," as used herein in reference to nucleic acids molecules encoding antibodies or antibody portions (e.g., VH, VL, CDRs) that bind to OspA, is intended to refer to a nucleic acid molecule in which the nucleotide sequences encoding the antibody or antibody portion are free of other nucleotide sequences encoding antibodies that bind antigens other than OspA, which other sequences may naturally flank the nucleic acid in human genomic DNA.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D.

All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, the terms "specific binding," "selective binding," "selectively binds," and "specifically binds," refer to antibody binding to an epitope on a predetermined antigen. Typically, the antibody binds with an affinity ($K_D$) of approximately less than $10^{-7}$ M, such as approximately less than $10^{-8}$ M, $10^{-9}$ M or $10^{-10}$ M or even lower when determined by surface plasmon resonance (SPR) technology in a BIACORE 3000 instrument, which can be performed, for example, using recombinant OspA as the analyte and the antibody as the ligand. In some embodiments, binding by the antibody to the predetermined antigen is with an affinity that is at least two-fold greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen."

A "subject" or an "individual" is a mammal. Mammals include, but are not limited to, domesticated animals (e.g., cows, sheep, cats, dogs, and horses), primates (e.g., humans and non-human primates such as monkeys), rabbits, deer, and rodents (e.g., mice and rats). In certain embodiments, the subject or individual is a human.

The terms "treat," "treating," and "treatment," as used herein, refer to preventative or therapeutic measures described herein. The methods of "treatment" employ administration to a subject in need of such treatment an antibody of the present invention, for example, a subject at risk of developing a disorder associated with a *Borrelia* infection or a subject having a disorder associated with a *Borrelia* infection, in order to prevent, cure, delay, reduce the severity of, or ameliorate one or more symptoms of the disorder or recurring disorder, or in order to prolong the survival of a subject beyond that expected in the absence of such treatment. In some embodiments, for example, the anti-OspA antibodies of the invention would be administered (e.g., at the beginning of tick season) to a subject at risk of developing a disorder associated with a *Borrelia* infection (e.g., a subject residing or traveling to a geographical location in which pathogenic *Borrelia* and *Borrelia* vector(s) are found). In instances in which the *Borrelia* vector is a tick of the genus *Ixodes*, when the tick takes a blood meal from a subject to whom one or more anti-OspA antibodies of the invention were administered, the anti-OspA antibodies bind to OspA expressed on the surface of *Borrelia* that have migrated from the midgut of the tick towards its mouth (e.g., to its salivary glands) and kill the *Borrelia* before the bacteria can move to the mouth of the tick and infect the subject. Accordingly, desirable effects of treatment include, but are not limited to, preventing occurrence of disease or disorder, such as a disorder associated with a *Borrelia* infection. Other desirable effects of treatment may include preventing recurrence of disease, alleviation of symptoms, diminishment of any direct or indirect pathological consequences of the disease, decreasing the rate of disease progression, amelioration or palliation of the disease state, and improved prognosis.

As used herein, "administering" is meant a method of giving a dosage of a compound (e.g., an anti-OspA antibody of the invention or a nucleic acid encoding an anti-OspA antibody of the invention) or a composition (e.g., a pharmaceutical composition, e.g., a pharmaceutical composition including an anti-OspA antibody of the invention) to a subject. The compositions utilized in the methods described herein can be administered, for example, intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, in cremes, or in lipid compositions. The method of administration can vary depending on various factors (e.g., the compound or composition being administered and the severity of the condition, disease, or disorder being treated).

As used herein, the term "vector" is meant to include, but is not limited to, a nucleic acid molecule (e.g., a nucleic acid molecule that is capable of transporting another nucleic acid to which it has been linked), a virus (e.g., a lentivirus or an adenovirus, e.g., a recombinant adeno-associated virus (rAAV)), cationic lipid (e.g., liposome), cationic polymer (e.g., polysome), virosome, nanoparticle, or dentrimer. Accordingly, one type of vector is a viral vector, wherein additional DNA segments (e.g., transgenes, e.g., transgenes encoding the heavy and/or light chain genes of an anti-OspA antibody of the invention) may be ligated into the viral genome, and the viral vector may then be administered (e.g., by electroporation, e.g., electroporation into muscle tissue) to the subject in order to allow for transgene expression in a manner analogous to gene therapy. Another type of vector is a "plasmid," which refers to a circular double stranded DNA loop into which additional DNA segments may be ligated. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids.

II. Compositions and Methods

In one aspect, the invention is based, in part, on anti-OspA antibodies. Antibodies of the invention are useful, for example, for treating a subject having, or at risk of developing, a disorder associated with a *Borrelia* infection.

A. Anti-OspA Antibodies

The invention provides isolated antibodies that bind to the outer surface protein A (OspA) of *Borrelia*.

In one aspect, the invention provides isolated antibody that specifically binds to outer surface protein A (OspA), wherein the antibody binds to an epitope comprising amino acid residues 71-141 of OspA (SEQ ID NO: 1), or an epitope comprising amino acid residues having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99 identity) to SEQ ID NO: 1. In some instances, the antibody includes the following complementarity determining regions (CDRs): (a) a CDR-H1 comprising the amino acid sequence of GYX$_1$FX$_2$SYWIG, wherein X$_1$ is S or K and X$_2$ is T or S (SEQ ID NO: 2); (b) a CDR-H2 comprising the amino acid sequence of X$_1$IX$_2$PGDSDX$_3$RYSPSFQG, wherein X$_1$ is F or I, X$_2$ is Y or F, and X$_3$ is T or K (SEQ ID NO: 3); and (c) a CDR-H3 comprising the amino acid sequence of ARGILRYFDWFLDY (SEQ ID NO: 4) or ARHITTHTYRGFFDF (SEQ ID NO: 5), or a combination of one or more of the above CDRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 2, 3, 4, and/or 5. In some instances, the antibody includes the following CDRs: (a) a CDR-L1 comprising the amino acid sequence of RASQX$_1$ISSX$_2$X$_3$A, wherein X$_1$ is G or D, X$_2$ is G or A, and X$_3$ is S or L (SEQ ID NO: 6); (b) a CDR-L2 comprising the amino acid sequence of DVSSLES (SEQ ID NO: 7); and (c) a CDR-L3 comprising the amino acid sequence of QQFNSYLLT (SEQ ID NO: 8) or QQFNGYPHRLT (SEQ ID NO: 9), or a combination of one or more of the above CDRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 6, 7, 8, and/or 9.

In some instances, the antibody includes the following six CDRs: (a) a CDR-H1 comprising the amino acid sequence of GYX$_1$FX$_2$SYWIG, wherein X$_1$ is S or K and X$_2$ is T or S (SEQ ID NO: 2); (b) a CDR-H2 comprising the amino acid sequence of X$_1$IX$_2$PGDSDX$_3$RYSPSFQG, wherein X$_1$ is F or I, X$_2$ is Y or F, and X$_3$ is T or K (SEQ ID NO: 3); (c) a CDR-H3 comprising the amino acid sequence of ARGILRYFDWFLDY (SEQ ID NO: 4) or ARHITTHTYRGFFDF (SEQ ID NO: 5); (d) a CDR-L1 comprising the amino acid sequence of RASQX$_1$ISSX$_2$X$_3$A, wherein X$_1$ is G or D, X$_2$ is G or A, and X$_3$ is S or L (SEQ ID NO: 6); (e) a CDR-L2 comprising the amino acid sequence of DVSSLES (SEQ ID NO: 7); and (f) a CDR-L3 comprising the amino acid sequence of QQFNSYLLT (SEQ ID NO: 8) or QQFNGYPHRLT (SEQ ID NO: 9), or a combination of one or more of the above CDRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 2-9.

For example, the antibody may include the following six CDRs: (a) a CDR-H1 comprising the amino acid sequence of GYSFTSYWIG (SEQ ID NO: 10); (b) a CDR-H2 comprising the amino acid sequence of FIYPGDSDTRYSPSFQG (SEQ ID NO: 11); (c) a CDR-H3 comprising the amino acid sequence of ARGILRYFDWFLDY (SEQ ID NO: 4); (d) a CDR-L1 comprising the amino acid sequence of RASQGISSGSA (SEQ ID NO: 12); (e) a CDR-L2 comprising the amino acid sequence of DVSSLES (SEQ ID NO: 7); and (f) a CDR-L3 comprising the amino acid sequence of QQFNSYLLT (SEQ ID NO: 8), or a combination of one or more of the above CDRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 2-9. In some instances, the antibody comprises (a) a heavy chain variable domain (VH) sequence having at least 90% sequence identity (e.g., at least 91%, 92%, 93%, 94%, 95%, 96%, 97%, 98%, or 99% sequence identity) to, or the sequence of, SEQ ID NO: 13; (b) a light chain variable domain (VL) sequence having at least 90% sequence identity (e.g., at least 91%, 92%, 93%, 94%, 95%, 96%, 97%, 98%, or 99% sequence identity) to, or the sequence of, SEQ ID NO: 14; or (c) a VH sequence as in (a) and a VL sequence as in (b). In some instances, the antibody binds to an epitope comprising amino acid residues 71-105 of OspA (SEQ ID NO: 15), or an epitope comprising amino acid residues having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99 identity) to SEQ ID NO: 15. In particular instances, the antibody is the exemplary anti-OspA antibody 221-7.

In another example, the antibody may include the following six CDRs: (a) a CDR-H1 comprising the amino acid sequence of GYKFSSYWIG (SEQ ID NO: 16); (b) a CDR-H2 comprising the amino acid sequence of IIFPGDSDKRYSPSFQG (SEQ ID NO: 17); (c) a CDR-H3 comprising the amino acid sequence of ARHITTHTYRGFFDF (SEQ ID NO: 5); (d) a CDR-L1 comprising the amino acid sequence of RASQDISSALA (SEQ ID NO: 18); (e) a CDR-L2 comprising the amino acid sequence of DVSSLES (SEQ ID NO: 7); and (f) a CDR-L3 comprising the amino acid sequence of QQFNGYPHRLT (SEQ ID NO: 9), or a combination of one or more of the above CDRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 5, 7, 9, and 16-18. In some instances, the antibody comprises (a) a heavy chain variable domain (VH) sequence having at least 90% sequence identity (e.g., at least 91%, 92%, 93%, 94%, 95%, 96%, 97%, 98%, or 99% sequence identity) to, or the sequence of, SEQ ID NO: 19; (b) a light chain variable domain (VL) sequence having at least 90% sequence identity (e.g., at least 91%, 92%, 93%, 94%, 95%, 96%, 97%, 98%, or 99% sequence identity) to, or the sequence of, SEQ ID NO: 20; or (c) a VH sequence as in (a) and a VL sequence as in (b). In some instances, the antibody binds to an epitope comprising amino acid residues 106-141 of OspA (SEQ ID NO: 21), or an epitope comprising amino acid residues having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99 identity) to SEQ ID NO: 21. In particular instances, the antibody is the exemplary anti-OspA antibody 857-2.

In some instances, the antibody may bind to three or more (e.g., 3, 4, 5, 6, or 7 or more) *Borrelia* species. In some instances, the three or more *Borrelia* species comprises *Borrelia burgdorferi*, *Borrelia afzelii*, and *Borrelia garinii*. In some instances, the antibody may bind to OspA of *Borrelia burgdorferi*, *Borrelia afzelii*, and *Borrelia garinii* with a $K_D$ of at least about 50 nM or lower (e.g., at least about 40 nM or lower, e.g., at least about 10 nM or lower, e.g., at least about 7.8 nM or lower, e.g., at least about 1.6 nM or lower). The antibody may also exhibit borreliacidal activity against *Borrelia* species comprising *Borrelia burgdorferi*, *Borrelia afzelii*, and *Borrelia garinii* in a borreliacidal assay and/or inhibit a *Borrelia* infection in vivo in a subject (e.g., a *Borrelia burgdorferi*, *Borrelia afzelii*, and/or *Borrelia garinii* infection).

In another aspect of the invention, the invention provides isolated antibody that specifically binds to OspA, wherein the antibody binds to an epitope comprising amino acid residues 178-273 of OspA (SEQ ID NO: 22), or an epitope comprising amino acid residues having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99 identity) to SEQ ID NO: 22. In some instances, the antibody includes the following complementarity determining regions (CDRs): (a) a CDR-H1 comprising the amino acid sequence of GYIFATYWIG (SEQ ID NO: 23); (b) a CDR-H2 comprising the amino acid sequence of IIYPNDSDTRYSPSFQG (SEQ ID NO: 24); and (c) a CDR-H3 comprising the amino acid sequence of ARTRWYFDL (SEQ ID NO: 25), or a combination of one or more of the above CDRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 23-25. In some instances, the antibody includes the following CDRs: (a) a CDR-L1 comprising the amino acid sequence of RASQSVSSSYLA (SEQ ID NO: 26); (b) a CDR-L2 comprising the amino acid sequence of GASSRAT (SEQ ID NO: 27); and (c) a CDR-L3 comprising the amino acid sequence of QQYGSSPLT (SEQ ID NO: 28), or a combination of one or more of the above CDRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 26-28.

In some instances, the antibody includes the following six CDRs: (a) a CDR-H1 comprising the amino acid sequence of GYIFATYWIG (SEQ ID NO: 23); (b) a CDR-H2 comprising the amino acid sequence of IIYPNDSDTRYSPS-FQG (SEQ ID NO: 24); (c) a CDR-H3 comprising the amino acid sequence of ARTRWYFDL (SEQ ID NO: 25); (d) a CDR-L1 comprising the amino acid sequence of RASQS-VSSSYLA (SEQ ID NO: 26); (e) a CDR-L2 comprising the amino acid sequence of GASSRAT (SEQ ID NO: 27); and (f) a CDR-L3 comprising the amino acid sequence of QQYGSSPLT (SEQ ID NO: 28), or a combination of one or more of the above CDRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 23-28. In some instances, the antibody comprises (a) a heavy chain variable domain (VH) sequence having at least 90% sequence identity (e.g., at least 91%, 92%, 93%, 94%, 95%, 96%, 97%, 98%, or 99% sequence identity) to, or the sequence of, SEQ ID NO: 29; (b) a light chain variable domain (VL) sequence having at least 90% sequence identity (e.g., at least 91%, 92%, 93%, 94%, 95%, 96%, 97%, 98%, or 99% sequence identity) to, or the sequence of, SEQ ID NO: 30; or (c) a VH sequence as in (a) and a VL sequence as in (b). In particular instances, the antibody is the exemplary anti-OspA antibody 319-44.

In some instances, the antibody may bind to two or more (e.g., 2, 3, 4, 5, 6, or 7 or more) *Borrelia* species. In some instances, the two or more *Borrelia* species include *Borrelia burgdorferi* and *Borrelia afzelii*. In some instances, the antibody may bind to OspA of *Borrelia burgdorferi* and *Borrelia afzelii* with a $K_D$ of at least about 10 µM or lower (e.g., at least about 5 µM or lower, e.g., at least about 1.2 µM or lower). In some embodiments, the antibody may bind to OspA of *Borrelia burgdorferi* with a $K_D$ of at least about 350 nM or lower (e.g., at least about 328 nM or lower). In some instances, the two or more *Borrelia* species also includes *Borrelia garinii*, and the antibody may bind to OspA of *Borrelia garinii* and *Borrelia afzelii* with a $K_D$ of at least about 2 µM or lower (e.g., at least about 1.2 µM or lower). In some instances, the antibody may bind to OspA of *Borrelia garinii* with a $K_D$ of at least about 800 nM or lower (e.g., at least about 778 nM or lower). The antibody may also exhibit borreliacidal activity against *Borrelia* species including *Borrelia burgdorferi* and *Borrelia afzelii* in a borreliacidal assay and/or inhibit a *Borrelia* infection in vivo in a subject (e.g., a *Borrelia burgdorferi* and/or *Borrelia afzelii* infection).

In another aspect of the invention, the invention provides isolated antibody that specifically binds to OspA, wherein the antibody binds to an epitope comprising amino acid residues 142-177 of OspA (SEQ ID NO: 31), or an epitope comprising amino acid residues having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99 identity) to SEQ ID NO: 31. In some instances, the antibody includes the following complementarity determining regions (CDRs): (a) a CDR-H1 comprising the amino acid sequence of GFTFRNYWMD (SEQ ID NO: 32); (b) a CDR-H2 comprising the amino acid sequence of NIKQDGSVKYYVDSVEG (SEQ ID NO: 33); and (c) a CDR-H3 comprising the amino acid sequence of ARDGYS-GYDSVGFDI (SEQ ID NO: 34), or a combination of one or more of the above CDRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 32-34. In some instances, the antibody includes the following CDRs: (a) a CDR-L1 comprising the amino acid sequence of RASQSVSSSYLA (SEQ ID NO: 35); (b) a CDR-L2 comprising the amino acid sequence of DTSSRAT (SEQ ID NO: 36); and (c) a CDR-L3 comprising the amino acid sequence of QQYGSSPYT (SEQ ID NO: 37), or a combination of one or more of the above CDRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 35-37.

In some instances, the antibody includes the following six CDRs: (a) a CDR-H1 comprising the amino acid sequence of GFTFRNYWMD (SEQ ID NO: 32); (b) a CDR-H2 comprising the amino acid sequence of NIKQDGS-VKYYVDSVEG (SEQ ID NO: 33); (c) a CDR-H3 comprising the amino acid sequence of ARDGYSGYDSVGFDI (SEQ ID NO: 34); (d) a CDR-L1 comprising the amino acid sequence of RASQSVSSSYLA (SEQ ID NO: 35); (e) a CDR-L2 comprising the amino acid sequence of DTSSRAT (SEQ ID NO: 36); and (f) a CDR-L3 comprising the amino acid sequence of QQYGSSPYT (SEQ ID NO: 37), or a combination of one or more of the above CDRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 32-37. In some instances, the antibody comprises (a) a heavy chain variable domain (VH) sequence having at least 90% sequence identity (e.g., at least 91%, 92%, 93%, 94%, 95%, 96%, 97%, 98%, or 99% sequence identity) to, or the sequence of, SEQ ID NO: 38; (b) a light chain variable domain (VL) sequence having at least 90% sequence identity (e.g., at least 91%, 92%, 93%, 94%, 95%, 96%, 97%, 98%, or 99% sequence identity) to, or the sequence of, SEQ ID NO: 39; or (c) a VH sequence as in (a) and a VL sequence as in (b). In particular instances, the antibody is the exemplary anti-OspA antibody 212-55.

In some instances, the antibody may bind to one or more (e.g., 1, 2, 3, 4, 5, 6, or 7 or more) *Borrelia* species. In some instances, the one or more *Borrelia* species includes *Borrelia burgdorferi*. In some instances, the antibody may bind to OspA of *Borrelia burgdorferi* with a $K_D$ of at least about 100 nM or lower (e.g., at least about 50 nM or lower, e.g., at least about 22 nM or lower). In some embodiments, the antibody may also bind to OspA of *Borrelia garinii* with a $K_D$ of at least about 1 µM or lower (e.g., at least about 500 nM or lower, e.g., at least about 480 nM or lower). The antibody may also exhibit borreliacidal activity against *Borrelia* species including *Borrelia burgdorferi* in a borreliacidal assay and/or inhibit a *Borrelia* infection in vivo in a subject (e.g., a *Borrelia burgdorferi* infection).

Antibodies of the invention may, for example, be monoclonal, human, humanized, or chimeric. The antibodies can be full-length antibodies or antibody fragments thereof (e.g., an antibody fragment that binds OspA). The antibody fragment may be selected from the group consisting of Fab, Fab'-SH, Fv, scFv, and (Fab')$_2$ fragments. In some instances, the antibody is an IgG antibody (e.g., an IgG1 antibody). An antibody of the invention may have a half-life of ≥3 days (e.g., ≥1 week, e.g., ≥2 weeks, e.g., ≥1 month, e.g., ≥2 months, e.g., ≥3 months, e.g., ≥4 months, e.g., ≥5 months, e.g., ≥6 months).

In a further aspect, an anti-OspA antibody according to any of the above embodiments may incorporate any of the features, singly or in combination, as described in Sections 1-5 below.

1. Antibody Affinity

In certain embodiments, an antibody provided herein may have a dissociation constant ($K_D$) of ≤10 µM, ≤1 µM, ≤100 nM, ≤10 nM, ≤1 nM, ≤0.1 nM, or ≤0.01 nM.

In one embodiment, $K_D$ is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, $K_D$ is measured using a BIACORE® surface plasmon resonance assay. For example, an assay using a BIACORE®-3000 (BIAcore, Inc., Piscataway, N.J.) is performed at 25° C. with immobilized antigen CM5 chips at ~10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant ($K_D$) is calculated as the ratio $k_{on}/k_{off}$. See, for example, Chen et al., *J. Mol. Biol.* 293:865-881 (1999). If the on-rate exceeds $10^6 M^{-1} s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, which are known in the art. Also included are diabodies, which have two antigen-binding sites that may be bivalent or bispecific, as is known in the art. Triabodies and tetrabodies are also known. Single-domain antibodies are also antibody fragments comprising all or a portion of the heavy chain variable domain or all or a portion of the light chain variable domain of an antibody. In certain embodiments, a single-domain antibody is a human single-domain antibody.

Antibody fragments can be made by various techniques, including but not limited to proteolytic digestion of an intact antibody as well as production by recombinant host cells (e.g., *E. coli* or phage), as described herein.

3. Chimeric and Humanized Antibodies

In certain embodiments, an antibody provided herein is a chimeric antibody. In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA*, 89:4285 (1992); and Presta et al. *J. Immunol*, 151:2623 (1993)); human mature (somatically mutated) framework regions or human germ line framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody (e.g., a human monoclonal antibody (HuMab), e.g., an anti-OspA HuMab). Human antibodies can be produced using various techniques known in the art.

In some instances, human antibodies are obtained by cloning the heavy and light chain genes directly from human B cells obtained from a human subject. The B cells are separated from peripheral blood (e.g., by flow cytometry, e.g., FACS), stained for B cell marker(s), and assessed for antigen binding. The RNA encoding the heavy and light chain variable regions (or the entire heavy and light chains) is extracted and reverse transcribed into DNA, from which the antibody genes are amplified (e.g., by PCR) and sequenced. The known antibody sequences can then be used to express recombinant human antibodies against a known target antigen (e.g., OspA).

In some instances, human antibodies may be prepared by administering an immunogen (e.g., OspA) to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. Human variable regions from intact antibodies generated by such animals may be further modified, for example, by combining with a different human constant region.

In some instances, human antibodies can also be made by hybridoma-based methods, as described in further detail below. Human myeloma and mouse-human heteromyeloma cell lines for the production of human monoclonal antibodies have been described.

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Antibody Variants

In certain embodiments, amino acid sequence variants of the anti-OspA antibodies of the invention are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, for example, antigen-binding.

In certain embodiments, antibody variants having one or more amino acid substitutions are provided. Sites of interest for substitutional mutagenesis include the CDRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, for example, retained/improved antigen binding, decreased immunogenicity, or improved ADCC or CDC.

TABLE 1

Exemplary and Preferred Amino Acid Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |

TABLE 1-continued

Exemplary and Preferred Amino Acid Substitutions

| Original Residue | Exemplary Substitutions | Preferred Substitutions |
|---|---|---|
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more CDR residues are mutated and the variant antibodies displayed on phage and screened for a particular biological activity (e.g., binding affinity).

Alterations (e.g., substitutions) may be made in CDRs, for example, to improve antibody affinity. Such alterations may be made in CDR "hotspots," i.e., residues encoded by codons that undergo mutation at high frequency during the somatic maturation process, and/or residues that contact antigen, with the resulting variant VH or VL being tested for binding affinity. Affinity maturation by constructing and reselecting from secondary libraries is known in the art. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves CDR-directed approaches, in which several CDR residues (e.g., 4-6 residues at a time) are randomized. CDR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in CDRs. Such alterations may, for example, be outside of antigen contacting residues in the CDRs. In certain embodiments of the variant VH and VL sequences provided above, each CDR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) Science, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

In certain embodiments, alternations may be made to the Fc region of an antibody. These alterations can be made alone, or in addition to, alterations to one or more of the antibody variable domains (i.e., VH or VL regions) or regions thereof (e.g., one or more CDRs or FRs). The alterations to the Fc region may result in enhanced antibody effector functions (e.g., complement-dependent cytotoxicity (CDC)), for example, by increasing C1q avidity to opsonized cells. Exemplary mutations that enhance CDC include, for example, Fc mutations E345R, E430G, and S440Y. Accordingly, anti-OspA antibodies of the invention may contain one or more CDC-enhancing Fc mutations, which promote IgG hexamer formation and the subsequent recruitment and activation of C1, the first component of complement (see, e.g., Diebolder et al. Science. 343: 1260-1263, 2014).

In certain embodiments, alterations of the amino acid sequences of the Fc region of the antibody may alter the half-life of the antibody in the host. Certain mutations that alter binding to the neonatal Fc receptor (FcRn) may extend half-life of antibodies in serum. For example, antibodies that have tyrosine in heavy chain position 252, threonine in position 254, and glutamic acid in position 256 of the heavy chain can have dramatically extended half-life in serum (see, e.g., U.S. Pat. No. 7,083,784).

B. Production of Human Antibodies to *Borrelia* OspA

1. Immunizations

The present invention features human monoclonal antibodies (HuMabs) that bind OspA of *Borrelia*. Exemplary human monoclonal antibodies that bind *Borrelia* OspA include 221-7, 857-2, 319-44, and 212-55.

Human monoclonal antibodies of the invention can be produced using a variety of known techniques, such as the standard somatic cell hybridization technique described by Kohler and Milstein, Nature 256: 495 (1975). Although somatic cell hybridization procedures are preferred, in principle, other techniques for producing monoclonal antibodies also can be employed, e.g., viral or oncogenic transformation of B lymphocytes, phage display technique using libraries of human antibody genes.

The preferred animal system for generating hybridomas which produce human monoclonal antibodies of the invention is the murine system. Hybridoma production in the mouse is well known in the art, including immunization protocols and techniques for isolating and fusing immunized splenocytes.

In one embodiment, human monoclonal antibodies directed against Borrelia OspA are generated using transgenic mice carrying parts of the human immune system rather than the mouse system. In one embodiment, the invention employs transgenic mice, referred to herein as "HuMAb mice," which contain a human immunoglobulin gene miniloci that encodes unrearranged human heavy (μ and γ) and κ light chain immunoglobulin sequences, together with targeted mutations that inactivate the endogenous μ and κ chain loci. Accordingly, the mice exhibit reduced expression of mouse IgM or κ, and in response to immunization, the introduced human heavy and light chain transgenes undergo class switching and somatic mutation to generate high affinity human IgG κ monoclonal antibodies.

To generate fully human monoclonal antibodies to Borrelia OspA, transgenic mice containing human immunoglobulin genes and inactivated mouse heavy and kappa light chain genes (Bristol-Myers Squib) can be immunized with a purified or enriched preparation of the OspA antigen (e.g., OspA-Trx or OspA-GST) and/or cells expressing OspA, as described, for example, by Lonberg et al. (1994) Nature 368(6474): 856-859; Fishwild et al. (1996) Nature Biotechnology 14: 845-851 and WO 98/24884. As described herein, HuMAb mice are immunized either with recombinant OspA proteins or cell lines expressing OspA as immunogens. Alternatively, mice can be immunized with DNA encoding OspA. Preferably, the mice will be 6-16 weeks of age (e.g., 6-10 weeks of age) upon the first infusion. For example, a purified or enriched preparation (10-100 μg, e.g., 50 μg) of the recombinant OspA antigen can be used to immunize the HuMAb mice, for example, intraperitoneally. In the event that immunizations using a purified or enriched preparation of the OspA antigen do not result in antibodies, mice can also be immunized with cells expressing OspA proteins, e.g., a cell line, to promote immune responses.

Cumulative experience with various antigens has shown that the HuMAb transgenic mice respond best when initially immunized intraperitoneally (IP) or subcutaneously (SC) with antigen in complete Freund's adjuvant, followed by every other week IP/SC immunizations (up to a total of 10) with antigen in incomplete Freund's adjuvant. The immune response can be monitored over the course of the immunization protocol with plasma samples being obtained by retro-orbital or facial vein bleeds. The plasma can be screened by ELISA (as described below), and mice with sufficient titers of anti-OspA human immunoglobulin can be used for fusions. Mice can be boosted intravenously with antigen 3 days before sacrifice and removal of the spleen.

2. Generation of Hybridomas Producing HuMabs to OspA

To generate hybridomas producing human monoclonal antibodies to OspA, splenocytes and lymph node cells from immunized mice can be isolated and fused to an appropriate immortalized cell line, such as a mouse myeloma cell line (e.g., P3X-AG8.653). The resulting hybridomas can then be screened for the production of antigen-specific antibodies. For example, single cell suspensions of splenic lymphocytes from immunized mice can be fused to SP2/0-AG8.653 non-secreting mouse myeloma cells (ATCC, CRL 1580) with 50% PEG (w/v). Cells can be plated at approximately $1 \times 10^5$ in flat bottom microtiter plate, followed by a two week incubation in selective medium containing besides usual reagents 10% fetal Clone Serum, and 1×HAT (Sigma). After approximately two weeks, cells can be cultured in medium in which the HAT is replaced with HT. Individual wells can then be screened by ELISA for human anti-OspA monoclonal IgM and IgG antibodies, or for binding to the surface of Borrelia expressing OspA proteins by, for example, FLISA (fluorescence-linked immunosorbent assay). Once extensive hybridoma growth occurs, medium can be observed usually after 10-14 days. The antibody secreting hybridomas can be re-plated, screened again, and, if still positive for human IgG, anti-OspA monoclonal antibodies can be subcloned at least twice by limiting dilution. The stable subclones can then be cultured in vitro to generate antibody in tissue culture medium for characterization.

3. Generation of Transfectomas Producing HuMabs to OspA

Human antibodies of the invention also can be produced in a host cell transfectoma using, for example, a combination of recombinant DNA techniques and gene transfection methods as is well known in the art. For example, in one embodiment, the gene(s) of interest, e.g., human antibody genes, can be ligated into an expression vector such as a eukaryotic expression plasmid. The purified plasmid with the cloned antibody genes can be introduced in eukaryotic host cells such as CHO-cells or NSO-cells or alternatively other eukaryotic cells like a plant derived cells, fungi or yeast cells. The method used to introduce these genes can be methods described in the art such as electroporation, lipofectine, lipofectamine or other. After introducing these antibody genes in the host cells, cells expressing the antibody can be identified and selected. These cells represent the transfectomas which can then be amplified for their expression level and upscaled to produce antibodies. Recombinant antibodies can be isolated and purified from these culture supernatants and/or cells. Alternatively these cloned antibody genes can be expressed in other expression systems such as E. coli or in complete organisms or can be synthetically expressed.

4. Recombinant Generation of HuMabs to OspA

Anti-OspA antibodies of the invention (e.g., anti-OspA antibodies 221-7, 857-2, 319-44, and 212-55, or variants thereof) may be produced using recombinant methods and compositions, for example, as described in U.S. Pat. No. 4,816,567. In one embodiment, isolated nucleic acid encoding an anti-OspA antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-OspA antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-OspA antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts.

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals *N.Y. Acad. Sci.* 383:44-68 (1982); MRC 5 cells; and FS4 cells. Other useful mammalian host cell lines include Chinese hamster ovary (CHO) cells, including DHFR⁻ CHO cells, and myeloma cell lines such as Y0, NS0 and Sp2/0.

C. Characterization of Human Monoclonal Antibodies to OspA

Sequence information for human monoclonal antibodies of the invention can be ascertained using sequencing techniques which are well known in the art.

Similarly, affinity of the antibodies for *Borrelia* OspA can also be assessed using standard techniques. For example, Biacore 3000 can be used to determine the affinity of HuMabs to OspA (e.g., OspA-*burgdorferi*, OspA-*garinii*, and/or OspA-*afzelii*). HuMabs are captured on the surface of a Biacore chip (GE healthcare), for example, via amine coupling (Sensor Chip CM5). The captured HuMabs can be exposed to various concentrations of OspA in solution, and the $K_{on}$ and $K_{off}$ for an affinity ($K_D$) can be calculated, for example, by BIAevaluation software.

Human monoclonal antibodies of the invention can also be characterized for binding to *Borrelia* OspA using a variety of known techniques, such as ELISA, Western blot, etc. Generally, the antibodies are initially characterized by ELISA. Briefly, microtiter plates can be coated with purified OspA in PBS, and then blocked with irrelevant proteins such as bovine serum albumin (BSA) diluted in PBS. Dilutions of plasma from OspA-immunized mice are added to each well and incubated for 1-2 hours at 37° C. The plates are washed with PBS/Tween 20 and then incubated with a goat-anti-human IgG Fc-specific polyclonal reagent conjugated to alkaline phosphatase for 1 hour at 37° C. After washing, the plates are developed with ABTS substrate, and analyzed at OD of 405. Preferably, mice which develop the highest titers will be used for fusions.

In some instances, an ELISA assay as described above can be used to screen for antibodies and, thus, hybridomas that produce antibodies that show positive reactivity with the OspA immunogen. Hybridomas that bind, preferably with high affinity, to OspA can then be subcloned and further characterized. One clone from each hybridoma, which retains the reactivity of the parent cell (by ELISA), can then be chosen for making a cell bank, and for antibody purification.

In some instances, antibodies are evaluated for binding to the bacterial surface of one or more *Borrelia* species with a borreliacidal assay using a spirochete surface staining assay. Briefly, *Borrelia* culture is resuspended in an wash/incubation buffer (e.g., PBS+10% BSK-H) and incubated with the anti-OspA antibody for testing. The cells are washed following incubation and incubated with a fluorescently labeled secondary anti-human or anti-mouse IgG detection antibody (e.g., IgG-phycoerythrin; Jackson Immunoresearch). Cells are again washed twice with wash/incubation buffer and fluorescence is analyzed (e.g., using a FACScan instrument with CellQuest software (Becton Dickinson)).

In other instances, competition assays may be used to identify an antibody that competes with an anti-OspA antibody of the invention for binding to OspA. In certain embodiments, such a competing antibody binds to the same epitope (e.g., a linear or a conformational epitope) that is bound by an anti-OspA antibody of the invention. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized OspA is incubated in a solution comprising a first labeled antibody that binds to OspA and a second unlabeled antibody that is being tested for its ability to compete with the first antibody for binding to OspA. The second antibody may be present in a hybridoma supernatant. As a control, immobilized OspA is incubated in a solution comprising the first labeled antibody but not the second unlabeled antibody. After incubation under conditions permissive for binding of the first antibody to OspA, excess unbound antibody is removed, and the amount of label associated with immobilized OspA is measured. If the amount of label associated with immobilized OspA is substantially reduced in the test sample relative to the control sample, then that indicates that the second antibody is competing with the first antibody for binding to OspA.

In other instances, assays are provided to evaluate the borreliacidal activities of anti-OspA antibodies with a borreliacidal assay using Bac-Titer Glo detection. Briefly, the one or more *Borrelia* spirochete species (e.g., *B. burgdorferi* B31, *B. garinii* PBi and *B. afzelii* BO23) are separately cultured in medium (e.g., BSK-H Complete Medium (Sigma-Aldrich)), and working cell banks are generated for each species to keep low passage numbers. Frozen suspensions of *Borrelia* are thawed and inoculated into fresh BSK-H and incubated at 37° C. for 72 hours prior to the assay. Serial dilutions of the tested anti-OspA antibodies are made in a molded 96-well microtiter plate and *Borrelia* culture at a fixed concentration is added to each well to mix with antibodies. The microtiter plate is incubated and spirochete viability is subsequently quantified by luciferase detection with Bac-Titer Glo reagent (Promega). The resulting fluorescence of each well can be plotted and the half maximal effective concentration (EC50) value can be calculated by standard means.

D. Pharmaceutical Compositions

In another aspect, the present invention provides a composition, e.g., a pharmaceutical composition, containing one or more (e.g., 1, 2, 3, or 4 or more) of the anti-OspA human monoclonal antibodies (HuMabs), or antibody fragments thereof, of the present invention. The pharmaceutical compositions may be formulated together with a pharmaceutically acceptable carrier, excipient, or diluent. In some instances, the pharmaceutical compositions include two or more of the anti-OspA HuMabs of the invention. Preferably, each of the antibodies of the composition binds to a distinct, pre-selected epitope of OspA of *Borrelia*.

A pharmaceutical composition of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Pharmaceutical compositions of the invention also can be administered in combination therapy, i.e., combined with other agents. For example, the combination therapy can include a composition of the present invention with at least one or more additional therapeutic agents as necessary for the particular indication (e.g., Lyme disease) being treated.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions.

Sustained-release preparations may be prepared. Suitable examples of sustained-release preparations include semipermeable matrices of solid hydrophobic polymers containing the antibody, which matrices are in the form of shaped articles, for example, films, or microcapsules.

The formulations to be used for in vivo administration are generally sterile. Sterility may be readily accomplished, e.g., by filtration through sterile filtration membranes. Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof. Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants, such as TWEEN® 80. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Alternatively, genes encoding the anti-OspA antibodies of the invention may be delivered directly into the subject for expression rather than administering purified antibodies for prevention or therapy. For example, viral vectors, such as recombinant viruses, can be used to deliver the heavy and light chain genes. In one example, rAAV virus particles can be used to deliver anti-HIV monoclonal antibodies (Balazs et al. *Nature.* 481: 81, 2012). Antibody genes could also be effectively delivered by electroporation of muscle cells with plasmid DNA containing heavy and/or light chain genes (e.g., VH and/or VL genes) (Muthumani et al. *Hum Vaccin Immunother.* 10: 2253, 2013). Lentivirus vectors or other nucleic acids (e.g., RNA) capable of delivering transgenes could also be used to delivery antibody genes to establish serum antibody levels capable of prevention.

Also within the scope of the present invention are kits including human anti-OspA antibodies of the invention and, optionally, instructions for use. The kits can further contain one or more additional reagents, such as a second, different anti-OspA antibody having a complementary activity that binds to an epitope on OspA that is distinct from the epitope to which the first anti-OspA antibody binds.

E. Therapeutic Methods of the Invention

Any of the anti-OspA antibodies of the invention (e.g., HuMabs 221-7, 857-2, 319-44, and 212-55) and compositions containing the antibodies can be used in a variety of in vitro and in vivo therapeutic applications.

In one aspect, the invention features a method of treating a subject having a disorder associated with a *Borrelia* infection (e.g., Lyme disease) comprising administering a therapeutically effective amount of a monoclonal antibody (e.g., a human monoclonal antibody) that specifically binds to OspA or a pharmaceutical composition thereof, thereby treating the subject.

In another aspect, an anti-OspA antibody of the invention may be used in a method of treating a subject having a disorder associated with a *Borrelia* infection. In one embodiment, the method comprises administering to a subject having such a disorder associated with a *Borrelia* infection (e.g., Lyme borreliosis or Lyme disease) a therapeutically effective amount of one or more (e.g., 1, 2, 3, or 4 or more) anti-OspA antibodies of the invention or a pharmaceutical composition including the one or more anti-OspA antibodies.

In another aspect, an anti-OspA antibody of the invention may be used in a method of treating a subject at risk of developing a disorder associated with a *Borrelia* infection (e.g., treating a subject at risk of developing a disorder associated with a *Borrelia* infection with an anti-OspA antibody of the invention in order to prevent the subject from developing a disorder associated with a *Borrelia* infection, such as Lyme disease). In one embodiment, the method comprises administering to a subject at risk of developing a disorder associated with a *Borrelia* infection a therapeutically effective amount of one or more (e.g., 1, 2, 3, or 4 or more) anti-OspA antibodies of the invention or a pharmaceutical composition including the one or more anti-OspA antibodies. In some instances, a subject is at risk of a *Borrelia* infection following being bitten by a *Borrelia* vector, such as a tick of the genus *Ixodes*. In other instances, a subject can be considered at risk of a *Borrelia* infection if the subject is in a geographic region in which a *Borrelia* vector, such as the blacklegged tick *Ixodes scapularis*, is commonly found (e.g., the northeastern and upper midwestern United States). In other instances, subject can be considered at risk of a *Borrelia* infection if the subject had travelled, or will travel, to a geographic region in which a *Borrelia* vector, such as the blacklegged tick *Ixodes scapularis*, is commonly found.

Antibodies of the invention can be used either alone or in combination with other agents in a therapy. For instance, an antibody of the invention may be co-administered with at least one additional therapeutic agent. Such combination therapies encompass combined administration (where two or more therapeutic agents are included in the same or separate formulations), and separate administration, in which case, administration of the antibody of the invention can occur prior to, simultaneously, and/or following, administration of the additional therapeutic agent or agents. In one embodiment, administration of the anti-OspA antibody (e.g., HuMabs 221-7, 857-2, 319-44, and 212-55) and administration of an additional therapeutic agent occur within about one month, or within about one, two or three weeks, or within about one, two, three, four, five, or six days, of each other.

An antibody of the invention, such as HuMabs 221-7, 857-2, 319-44, and 212-55, (and/or any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. In certain instances, antibody genes (e.g., genes encoding any one or more of the anti-OspA antibodies of the invention could be administered as a gene therapy to produce the one or more anti-OspA antibodies in the subject using either DNA vectors or viral vectors (e.g., rAAV vectors). Dosing can be by any suitable route, for example, by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, such as Lyme disease, the appropriate dosage of an antibody of the invention (when used alone or in combination with one or more other additional therapeutic agents) will depend on the type of disease to be prevented/treated, the duration of effective antibody concentration required, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. A preferred dosing regimen for the antibody is one that will keep the protective dose high enough to last the duration of a tick season.

As a general proposition, the therapeutically effective amount of the anti-OspA antibody administered to human will be in the range of about 0.01 to about 100 mg/kg of patient body weight whether by one or more administrations. In some embodiments, the antibody used is about 0.01 to about 45 mg/kg, about 0.01 to about 40 mg/kg, about 0.01 to about 35 mg/kg, about 0.01 to about 30 mg/kg, about 0.01 to about 25 mg/kg, about 0.01 to about 20 mg/kg, about 0.01 to about 15 mg/kg, about 0.01 to about 10 mg/kg, about 0.1 to about 10 mg/kg, or about 1 to about 10 mg/kg administered one (single administration) or more times (multiple administrations, e.g., daily administrations). In one embodiment, an anti-OspA antibody described herein is administered to a human at a dose of about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg or about 1400 mg on day 1 of 21-day cycles. The dose may be administered as a single dose or as multiple doses (e.g., 2 or 3 doses), such as infusions. For repeated administrations over several days or longer, depending on the condition, the treatment would generally be sustained until a desired suppression of disease symptoms occurs. One exemplary dosage of the antibody would be in the range from about 0.01 mg/kg to about 10 mg/kg. Such doses may be administered intermittently, for example, every week or every three weeks (e.g., such that the patient receives from about two to about twenty, or, for example, about six doses of the anti-OspA antibody). An initial higher loading dose, followed by one or more lower doses may be administered. The progress of this therapy is easily monitored by conventional techniques and assays.

Actual dosage levels of the active ingredients in the pharmaceutical compositions of the present invention may be varied so as to obtain an amount of the active ingredient which is effective to achieve the desired therapeutic response and duration for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian can start doses of the compounds of the invention employed in the pharmaceutical composition at levels lower than that required in order to achieve the desired therapeutic effect and gradually increase the dosage until the desired effect is achieved. In general, a suitable daily dose of compositions of the invention will be that amount of the compound which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of therapeutic compositions may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. The liposomes may comprise one or more moieties which are selectively transported into specific cells or organs, thus enhance targeted drug delivery. Exemplary targeting moieties include folate or biotin (see, e.g., U.S. Pat. No. 5,416,016 to Low et al.); mannosides (Umezawa et al., (1988) Biochem. Biophys. Res. Commun. 153:1038); antibodies (P. G. Bloeman et al. (1995) FEBS Lett. 357:140; M. Owais et al. (1995) Antimicrob. Agents Chemother. 39:180); surfactant protein A receptor (Briscoe et al. (1995) Am. J. Physiol. 1233:134), different species of which may comprise the formulations of the inventions, as well as components of the invented molecules; p 120 (Schreier et al. (1994) J. Biol. Chem. 269:9090); see also K. Keinanen; M. L. Laukkanen (1994) FEBS Lett. 346:123; J. J. Killion; I. J. Fidler (1994) Immunomethods 4:273. In one embodiment of the invention, the therapeutic compounds of the invention are formulated in liposomes; in a more preferred embodiment, the liposomes include a targeting moiety. In a most preferred embodiment, the therapeutic compounds in the liposomes are delivered by bolus injection to a site proximal to the tumor or infection. The composition must be fluid to the extent that easy syringability exists. It must be stable under the conditions of manufacture and storage and must be preserved against the contaminating action of microorganisms such as bacteria and fungi.

In some instances, the antibody-based therapy may be combined with an additional therapy for more efficacious treatment (e.g., additive or synergistic treatment) of the subject. Accordingly, subjects treated with antibodies of the invention can be additionally administered (prior to, simultaneously with, or following administration of a human antibody of the invention) with another therapeutic agent which enhances or augments the therapeutic effect of the human antibodies.

F. Methods and Compositions for Diagnostics and Detection

In certain embodiments, any of the anti-OspA antibodies of the invention are useful for in vitro or in vivo detection of the presence of OspA in a biological sample. The term "detecting" as used herein encompasses quantitative or qualitative detection. In certain embodiments, a biological sample comprises a cell or tissue.

In one embodiment, an anti-OspA antibody for use in a method of diagnosis (e.g., diagnosis of a disorder associated with a *Borrelia* infection) or detection (e.g., detection of a *Borrelia* infection) is provided. In a further aspect, a method of detecting the presence of OspA in a biological sample is provided. In certain embodiments, the method comprises contacting the biological sample with an anti-OspA antibody as described herein under conditions permissive for binding of the anti-OspA antibody to OspA, and detecting whether a complex is formed between the anti-OspA antibody and OspA. Such method may be an in vitro or in vivo method.

In certain embodiments, labeled anti-OspA antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

G. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Other embodiments of the present invention are described in the following Examples. The present invention is further illustrated by the following examples which should not be construed as further limiting. The contents of Sequence Listing, figures and all references, patents and published patent applications cited throughout this application are expressly incorporated herein by reference.

III. Examples

The following are examples of methods and compositions of the invention. It is understood that various other embodiments may be practiced, given the general description provided above.

Example 1. Materials and Methods

The invention is further described in the following examples, which do not limit the scope of the invention described in the claims.

Synthesis of the Gene Encoding OspA

The nucleic acid sequences encoding OspA from *Borrelia burgdorferi*B31, *Borrelia afzelii*ACA-1, and *Borrelia garinii*PBi (Genbank accession number NP_045688, SEQ ID NO: 40; UniProtKB B8DY02, SEQ ID NO: 41; and UniProtKB Q6LBF1, SEQ ID NO: 42, respectively) were obtained through public gene databases. The nucleotide sequence was synthesized by Genewiz and cloned into either a pGEX-4T-3 GST vector or a pET45-His in-frame with the N-terminal GST tag or histidine (His) tag. The vectors were then sequenced to verify their correctness.

Generation of OspA Truncations and Point Mutants

The portion of OspA protein encoding the desired amino acids was PCR amplified using full-length OspA as template and cloned into a pET45-His vector using SacI and SalI in-frame with the N-terminal His tag. The vectors were then sequenced to verify their correctness. The generated constructs include the following OspA truncations.

OspA a.a. 18-273, SEQ ID NO: 43;
OspA a.a. 18-141, SEQ ID NO: 44;
OspA a.a. 18-177, SEQ ID NO: 45;
OspA a.a. 71-273, SEQ ID NO: 46;
OspA a.a. 106-273, SEQ ID NO: 47;
OspA a.a. 142-273, SEQ ID NO: 48; and
OspA a.a. 178-273, SEQ ID NO: 22.

Site-directed mutagenesis was performed using overlapping primers containing D249A and S250A point mutations to amplify full-length OspA (a.a. 18-273) from the pET45-OspA vector. The amplified DNA was digested with DpnI to remove the template DNA, transformed into bacteria, and screened by standard DNA sequencing technology to ensure intended mutation.

All cloned constructs were transformed into BL21-DE3 *E. coli* bacteria (Invitrogen) and expression was induced with 1 mM IPTG. Bacteria were lysed and the proteins were purified with Ni-NTA agarose (Invitrogen) and eluted with 250 mM imidazole (Sigma). Protein integrity and purity was evaluated by Coomassie stained SDS-PAGE and Western blot using mouse anti-His antibody.

ELISA

Dilutions of purified HuMabs were tested in ELISA for reactivity against various OspA truncations and point mutants. Briefly, 96-well plates were coated with various OspA proteins followed by incubation overnight at 4° C. Hybridoma supernatant or purified antibody was added to the 96-well plates and incubated for 1 hour at room temperature. Antibody binding was detected with anti-human alkaline phosphatase secondary antibody and PNPP substrate.

Affinity Determination

Biacore 3000 was used to determine the affinity of HuMabs to OspA-*burgdorferi*, OspA-*garinii* and OspA-*afzelii*. HuMabs was captured on the surface of a Biacore chip (GE healthcare) via amine coupling (Sensor Chip CM5). The captured Mabs were exposed to various concentrations of OspA in solution. The $K_{on}$ and $K_{off}$ for an affinity ($K_D$) were calculated by BIAevaluation software.

Mouse Immunizations

Transgenic mice containing human immunoglobulin genes and inactivated mouse heavy and kappa light chain genes (Bristol-Myers Squib) were immunized with OspA-His or OspA-GST. Mice were injected weekly with 50 µg of OspA protein mixed with the Sigma adjuvant system (Sigma) for a total of 6-10 weeks. Mouse serum was measured by ELISA for binding activity with OspA-His to determine the time for maximal response.

Splenic Fusions and Hybridoma Selection

Mice were sacrificed when the maximal serum response were reached. Hybridomas were generated by fusion of splenocytes and mouse myeloma cells (P3X-AG8.653) following a standard PEG fusion. Hybridoma supernatants were then screened for reactivity to OspA-His by ELISA and positive cell clones were expanded for antibody purification.

Isolation and Sequencing of Hybridoma Antibody Genes

The heavy chain variable regions were amplified from hybridoma cells by RT-PCR with a mixture of heavy chain gene-specific primers. The resulting PCR product was cloned into a mammalian expression vector in frame with human IgG1 constant region for antibody expression. The light chain gene sequence was determined by Rapid Amplification of cDNA Ends by PCR (RACE) with light chain specific primers. The product was cloned into the pCR2.1-TOPO vector (Life Technologies) for sequencing to determine the specific allele of light chain. Gene specific primers were then designed to amplify the light chain variable region from pCR2.1-TOPO for subsequent cloning into mammalian expression vectors.

Borreliacidal Assay by Bac-Titer Glo Detection

*Borrelia* spirochetes (*B. burgdorferi* B31, *B. garinii* PBi, and *B. afzelii* BO23) were obtained from ATCC (Cat#35210, BAA-2496 and 51992). The genome of *B. afzelii* BO23 was sequenced and confirmed to have the same OspA sequence as *B. afzelii* ACA-1. Spirochetes were cultured in BSK-H Complete Medium (Sigma-Aldrich) and working cell banks were generated for each strain to keep low passage numbers. Frozen suspensions of *Borrelia* were thawed and inoculated into fresh BSK-H medium and incubated at 37° C. for 72 hours prior to the assay. Spirochetes were counted using dark-field microscopy with a Petroff-Hausser counting chamber.

Serial dilutions of antibodies were made in 100 µl of BSK-H medium containing 10% of guinea pig complement (Sigma) in a molded 96-well microtiter plate (Thermo Scientific Nunc Edge 96-well Plate). 100 µL of *Borrelia* culture at a concentration of $5\times10^6$ spirochetes/mL were added to each well to mix with antibodies. The microtiter plate was incubated at 37° C. for 3 days. The spirochete viability was then quantified by luciferase detection with Bac-Titer Glo reagent (Promega) and read in a Victor3 multi-label counter (Applied Biosystems). The resulting fluorescence of each well was plotted, and the half maximal effective concentration (EC50) value was calculated.

Spirochete Surface Staining

Two mL of *Borrelia* culture at a concentration of $1\times10^7$ spirochetes/ml were spun down at 7500 rpm for 10 minutes and resuspended in 1 mL PBS+10% BSK-H. Cells were incubated with 12.5 µg/ml primary antibody for 1 hr at RT. Cells were washed twice in PBS+10% BSK-H and incubated with anti-human or anti-mouse IgG-phycoerythrin (Jackson Immunoresearch) at a 1:100 dilution for 1 hour at room temperature. Cells were again washed twice with PBS+10% BSK-H medium. The fluorescence analysis was performed using a FACScan instrument with CellQuest software (Becton Dickinson).

Example 2. Generation of Anti-OspA Monoclonal Antibodies

Seventeen transgenic mice containing human immunoglobulin genes and inactivated mouse heavy and kappa light chain genes (Bristol-Myers Squibb; Medarex HuMab mice) were immunized with *B. burgdorferi* Outer surface protein A (OspA) expressed with glutathione-S-transferase (GST) or histidine fusion tags. OspA was administered via the intraperitoneal route with RIBI or Alum as adjuvant. After 6-9 weeks of weekly immunization, all 17 mice produced a robust sera response to their respective immunogen as measured by serum ELISA. Twelve mice were chosen for fusion based on strong serum response to the OspA antigen. Splenocytes were isolated from the animals and fused to mouse myeloma (P3X-AG8.653) cells using standard spleen cell fusion methods. Clonal hybridomas were screened by ELISA for production of anti-OspA specific antibody. A total of 589 OspA reactive hybridomas were identified for further characterization.

Example 3. Antibody Heavy Chain Sequence Determination

RT-PCR was performed on all 589 positive hybridomas to determine the sequence of the heavy chain gene of OspA-reactive antibodies using a cocktail of primers targeting the variable region of the human heavy chain genes. Forward primers were designed to anneal to all human heavy chain genes expressed in the transgenic mouse, and the reverse primers were specific to human IgG1 constant region. The PCR products were sequenced and aligned based on sequences in the CDR3 of the heavy chain. 169 antibodies were considered to have unique CDR3 sequences and selected for further characterization.

Example 4. Antibody Borreliacidal Activity

Figure 1C:
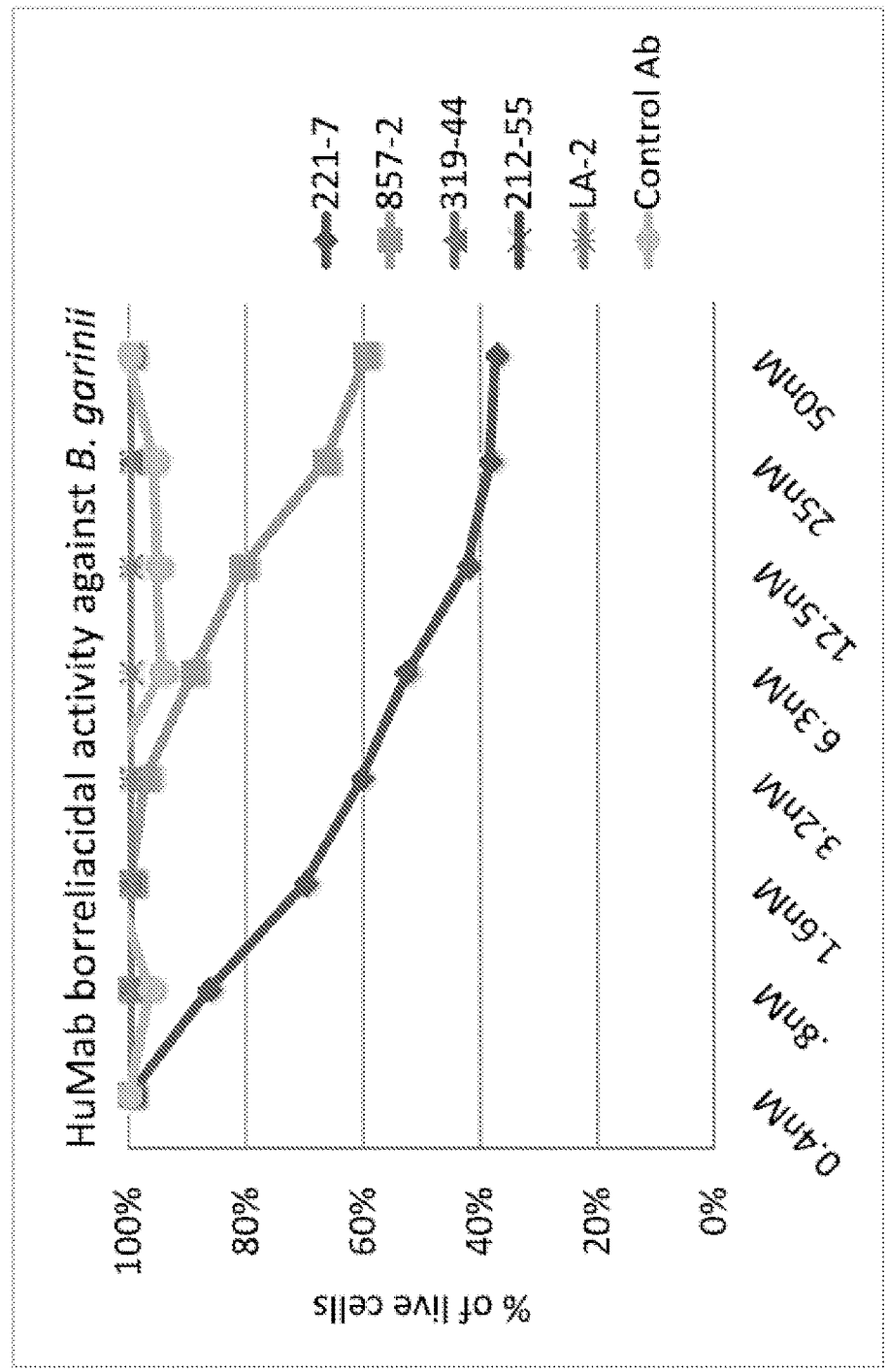
FIG. 1C is a graph showing the borreliacidal activities of anti-OspA HuMabs antibodies 221-7, 857-2, 319-44, and 212-55 against the *Borrelia* species *B. garinii* PBi, as compared to that of antibodies LA-2 and CDA1.

To determine antibody borreliacidal activity, 93 purified human monoclonal antibodies (HuMabs) were incubated with cultures of three strains of *Borrelia* spirochetes (*B. burgdorferi* B31, *B. garinii* PBi, and *B. afzelii* BO23) for three days at 37° C. The spirochete viability was quantified by Bac-Titer Glo assay kit. In this assay, the number of viable bacterial cells in culture was determined based on the amount of ATP present measured by a fluorescence dye. The resulting fluorescence intensity of each antibody and spirochete mixture was plotted and their half maximal effective concentration (EC50) value was calculated and used to rank HuMAb potency. Four HuMabs (antibodies 221-7, 857-2, 319-44, and 212-55), in particular, were selected as lead candidates based on their strong borreliacidal activity (<10 nM of IC50) against *B. burgdorferi* B31 (FIG. 1A). Antibodies 221-7 and 857-2 showed broader borreliacidal activity against *B. garinii* PBi and *B. afzelii* BO23 (FIGS. 1A-1C). Antibody 319-44 showed borreliacidal activity against *B. burgdorferi* B31 and *B. afzelii* BO23 (FIGS. 1A and 1B). Table 2 below summarizes the borreliacidal activity of each of the four lead HuMabs.

TABLE 2

EC50 value of borreliacidal activity of HuMabs against three *Borrelia* strains

| HuMAb | Borreliacidal activity (EC50 (nM)) | | |
|---|---|---|---|
|  | *B. burgdorferi* | *B. afzelii* | *B. garinii* |
| 221-7 | <0.4 | 0.9 | 6.6 |
| 857-2 | 2.0 | 2.0 | 41.6 |

TABLE 2-continued

EC50 value of borreliacidal activity of
HuMabs against three Borrelia strains

| HuMAb | Borreliacidal activity (EC50 (nM)) | | |
|---|---|---|---|
| | B. burgdorferi | B. afzelii | B. garinii |
| 319-44 | <0.4 | 4.0 | n/a |
| 212-55 | 1.4 | n/a | n/a |

Example 5. Antibody Epitope Mapping

Figures 2A, 2B:
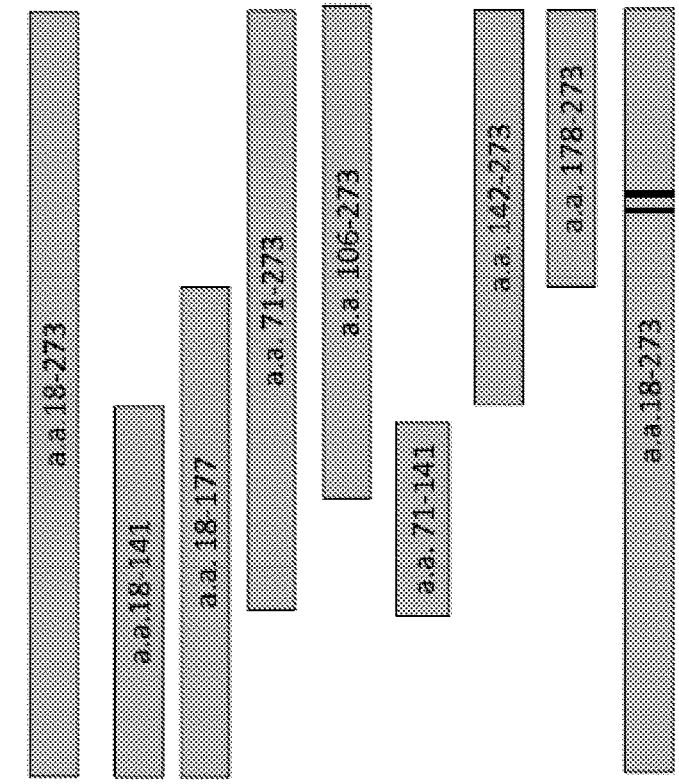
FIG. 2A shows the schematic map of a series of OspA proteins that were engineered and expressed as recombinant proteins for antibody epitope mapping studies.
FIG. 2B is a table showing the binding recognition of anti-OspA HuMabs antibodies 221-7, 857-2, 319-44, and 212-55, as well as anti-OspA antibody LA-2, to each of the OspA proteins of FIG. 2A. "+" indicates observed binding of the anti-OspA antibody to the tested OspA protein form. "−" indicates no observed binding of the anti-OspA antibody to the tested OspA protein form.
Figure 3:
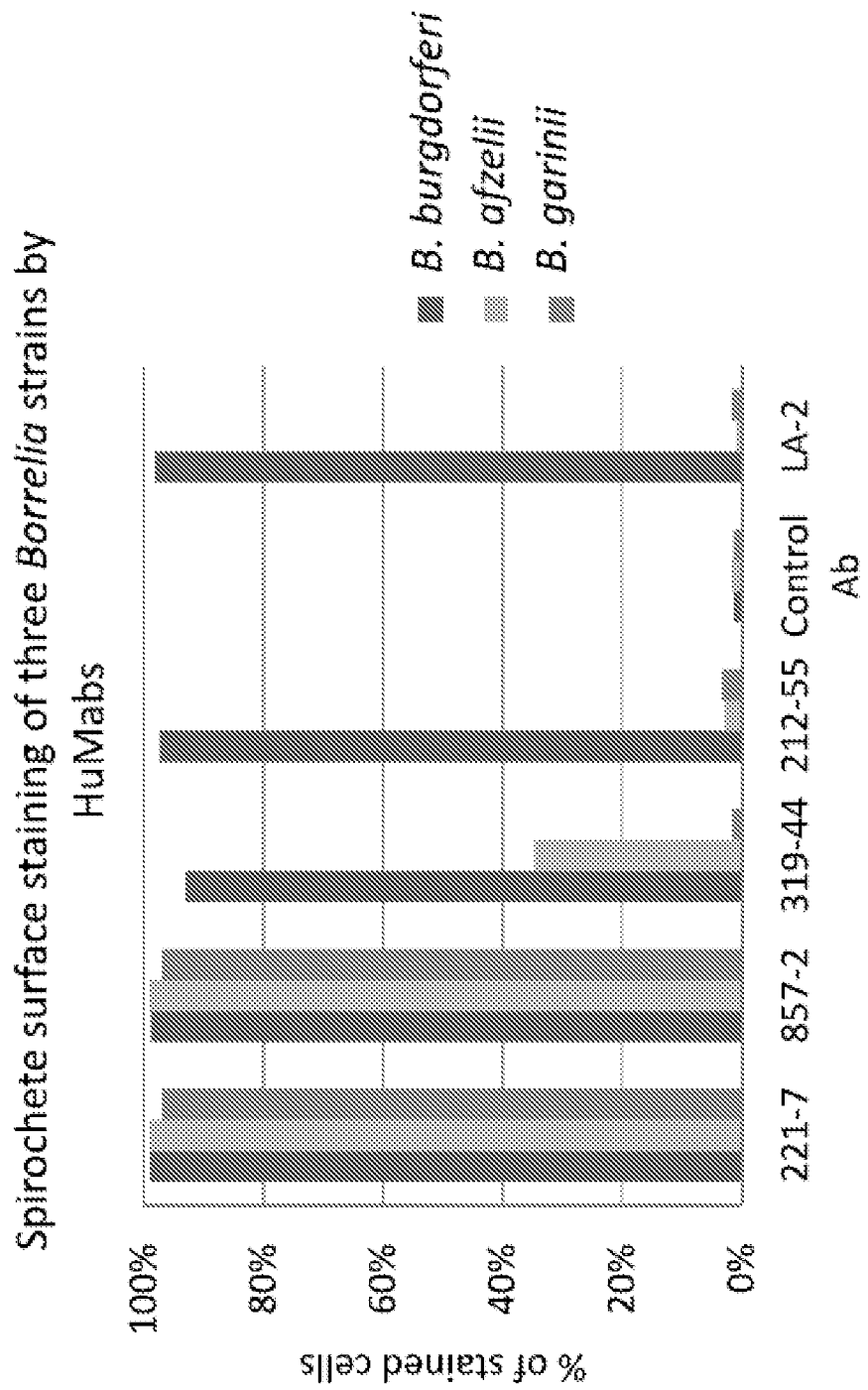
FIG. 3 is a graph showing the relative staining intensities (represented as total percentage of stained cells) by each of the anti-OspA HuMabs antibodies 221-7, 857-2, 319-44, and 212-55, as well as antibodies LA-2 and CDA1 in the spirochete surface staining assay.
Figures 4A, 4B:
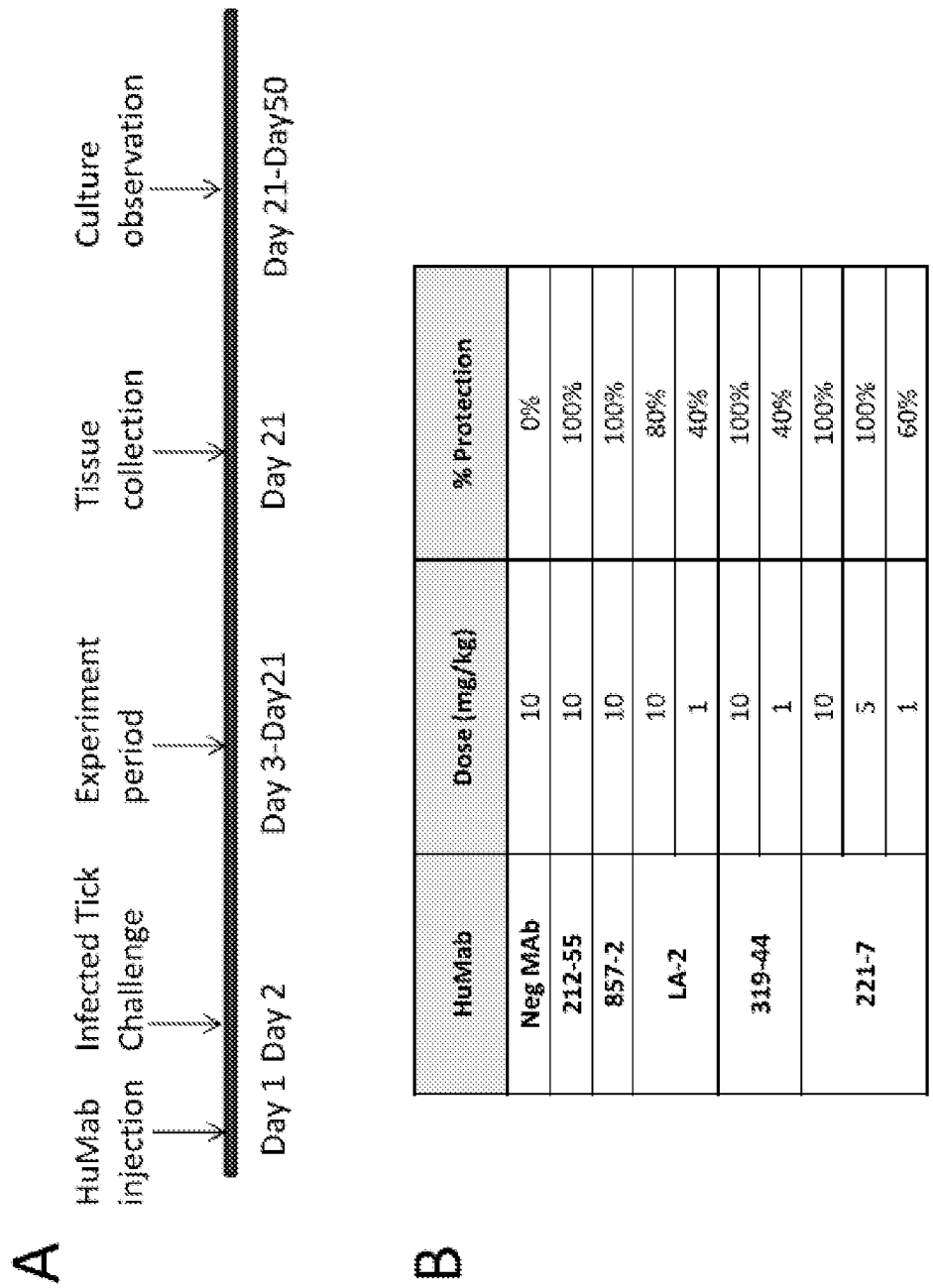
FIG. 4A is a schematic diagram showing the overall experimental design for the animal challenge experiments. Briefly, groups of individually housed C3H mice (n=5) were treated with one of the four lead HuMabs (antibodies 221-7, 857-2, 319-44, and 212-55), LA2, or a negative control MAb (Neg MAb) at a dose of 10 mg/kg on the first day. The next day, groups of individual mice were challenged by the placement of 6 infected tick nymphs behind the ear of each mouse and animals were housed individually to prevent tick removal by grooming. Mouse cages were placed in water moats for tick collection after their detachment from animals. Three weeks after the tick placement, mice were sacrificed and tissue samples from ear, bladder, heart, and (ankle) joint were harvested for *Borrelia* culture in BSK-H medium. Tissue samples were monitored twice weekly for 4 weeks by dark field microscopy for evidence of growth of *B. burgdorferi*. Animals were considered infected if viable *B. burgdorferi* was observed from any tissue sample during the 4-week observation period.
FIG. 4B is a table showing the results of the animal challenge experiments for each of the tested antibodies: 319-44, 212-55, 221-7, 857-2, LA-2, and Neg MAb.

To define the epitope of HuMabs 221-7, 857-2, 319-44, and 212-55, a series of OspA truncations and point mutations were engineered and expressed as recombinant proteins. ELISAs were performed for all four HuMabs for reactivity against various OspA recombinant protein forms (FIG. 2A). The HuMabs appear to recognize different fragments of OspA (FIG. 2B). Antibodies 221-7 and 857-2 both bound to an epitope located within amino acid residues 71-273 of OspA (e.g., an epitope including amino acid residues 71-141 of OspA). The epitope of 857-2 was further defined to a smaller epitope within amino acid residues 106-273 of OspA (e.g., an epitope including amino acid residues 106-141 of OspA). Antibody 212-55 bound to an epitope located within amino acid residues 142-273 of OspA (e.g., an epitope including amino acid residues 142-177 of OspA). The epitope of antibody 319-44 was found to be located within amino acid residues 178-273, a bactericidal epitope described previously for a mouse monoclonal antibody LA-2. Indeed, antibody 319-44 was able to compete with LA-2 for OspA binding.

To further distinguish the epitope between 319-44 and LA-2, an OspA mutant containing both D249A and S250A point mutations was generated based on structure prediction and tested on ELISA for antibody recognition. The alteration at amino acid D249A and S250A clearly disrupted binding for 319-44 but not LA-2, demonstrating that the residues required for 319-44 binding are different from those required for LA-2, even though 319-44 can compete with LA-2. Indeed, the 319-44 antibody requires one or both of the residues D249A and S250A for its binding to OspA. By contrast, binding of OspA by the LA-2 antibody does not require that the residues D249A and S250A be preserved; LA-2 exhibits binding to OspA whether the residues D249A and S250A are unmutated or mutated (e.g., D249A and S250A).

Example 6. Antibody Characterization

Spirochete Surface Staining

Three strains of *Borrelia* spirochetes (*B. burgdorferi* B31, *B. garinii* PBi, and *B. afzelii* BO23) were incubated with each of HuMabs 221-7, 857-2, 319-44, and 212-55, followed by phycoerythrin-conjugated anti-human secondary antibody to stain organisms. The fluorescence intensities were analyzed using a FACScan. All antibodies showed strong staining with *B. burgdorferi* B31 (FIG. 3). Antibodies 221-7 and 857-2 also stained with *B. garinii* PBi and *B. afzelii* BO23 species. Antibody 212-55 didn't stain *B. afzelii* BO23 or *B. garinii* PBi. Antibody 319-44 showed weak staining with *B. afzelii* BO23, but not with *B. garinii* PBi.

Antibody Affinity Determination

Affinity analyses were performed on HuMabs 221-7, 857-2, 319-44, and 212-55 by surface plasmon resonance (SPR) using a Biacore 3000 instrument. The affinities of the antibodies to three recombinant OspA proteins (OspA-*burgdorferi*, OspA-*garinii*, and OspA-*afzelii*) were determined (Table 3). As shown in Table 3 below, all four antibodies showed good binding to OspA-*burgdorferi*. Antibodies 221-7, 857-2, and 212-55 bound to OspA-*burgdorferi* with an affinity of at least 22 nM or better. Antibody 319-44 bound to OspA-*burgdorferi* with a weaker affinity of 328 nM. Antibodies 221-7 and 857-2 bound to all three OspA proteins, OspA-*burgdorferi*, OspA-*garinii*, and OspA-*afzelii*, with an affinity of at least 36 nM or better. Antibody 212-55 showed high affinity to OspA-*burgdorferi* but moderate affinity to OspA-*garinii*. The differences between these results and that of the spirochete surface staining data are possibly due to the structure difference between native and recombinant OspA proteins.

TABLE 3

Affinities of HuMabs for OspA proteins of three *Borrelia* species

| HuMAb | $K_D$ to OspA | | |
|---|---|---|---|
| | *B. burgdorferi* | *B. afzelii* | *B. garinii* |
| 221-7 | 0.66 nM | 7.8 nM | 1.3 nM |
| 857-2 | 0.65 nM | 1.6 nM | 1 nM |
| 319-44 | 328 nM | 1.2 μM | 674 nM |
| 212-55 | 0.43 nM | 3.8 μM | 480 nM |

Example 7. In Vivo Activity of Antibodies

Infected ticks were prepared for challenge study by placing *Ixodes dammini* (also known as *Ixodes scapularis*) larva on *B. burgdorferi*-infected SCID mice for a blood meal. Larvae were harvested and allowed to molt to the nymphal stage before used to challenge C3H mice (Charles River Laboratories). The experimental design for animal challenge is summarized in FIG. 4A. Groups of individually housed C3H mice (n=5) were treated with one of the four lead HuMabs (319-44, 212-55, 221-7 or 857-2), LA2, or a negative control monoclonal antibody (Neg MAb) at a dose of 10, 5, or 1 mg/kg on the first day, as indicated in FIG. 4B. The next day, groups of individual mice were challenged by the placement of 6 infected tick nymphs behind the ear of each mouse, and animals were housed individually to prevent tick removal by grooming. Mouse cages were placed in water moats for tick collection after their detachment from animals. Three weeks after the tick placement, mice were sacrificed and tissue samples from ear, bladder, heart, and (ankle) joint were harvested for *Borrelia* culture in BSK-H medium. Tissue samples were monitored twice weekly for 4 weeks by dark field microscopy for evidence of growth of *B. burgdorferi*. Animals were considered infected if viable *B. burgdorferi* was observed from any tissue sample during the 4-week observation period. Serum was collected at the time of sacrifice to confirm the presence of MAbs. The results are summarized in FIG. 4B. All animals that received the negative control antibody were infected. No animals treated with 10 mg/kg of HuMabs 319-44, 212-55, 221-7 or 857-2 were infected. 221-7 showed 100% animal protection at the lower dose of 5 mg/kg. Both 221-7 and 319-44 partially protected animals from infection at 1 mg/kg. These results suggest that HuMabs 319-44, 212-55, 221-7, and 857-2 can each prevent the transmission of *B. burgdorferi* from ticks to mice host in this model. We expect that these antibodies would have the same affect in other tick hosts, such as humans or companion animals.

Figure 5:
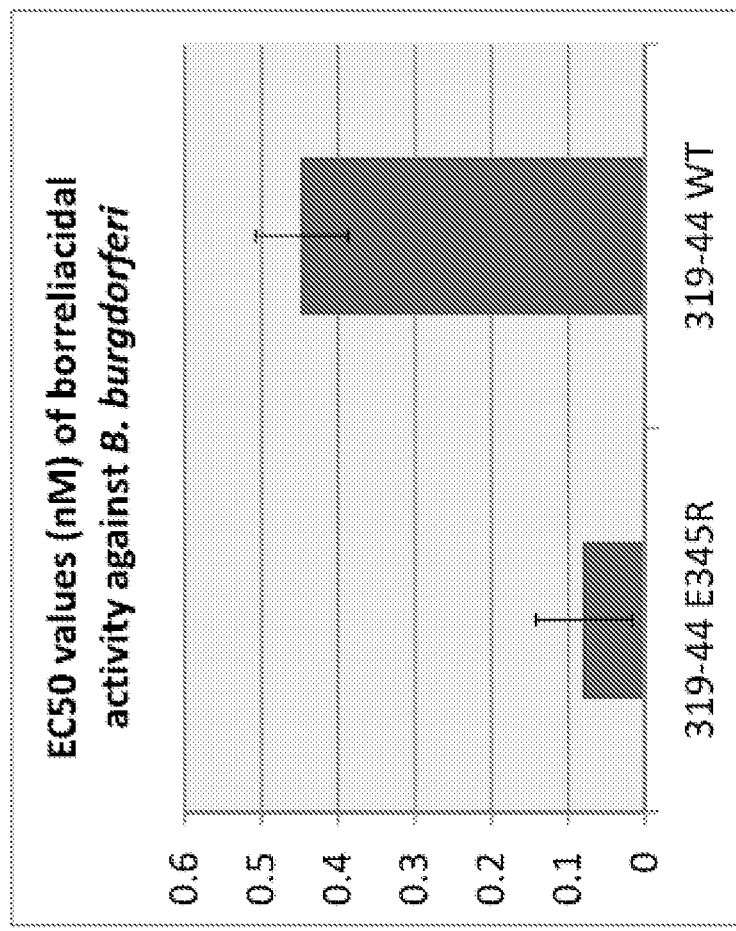
FIG. 5 is a graph showing the enhanced borreliacidal activity of the 319-44 E345R mutant antibody, as compared to that of the 319-44 wild-type antibody in the presence of complement.

Example 8. Enhanced Borreliacidal Activity In Vitro with Complement Activity-Enhancing Mutation To investigate the role of complement in protection, a complement activity-enhancing mutation, E345R, was introduced into the Fc region of antibody 319-44 by site-directed mutagenesis. The mutant construct was tested in the borreliacidal assay against *B. burgdorferi*. In the presence of complement, the in vitro borreliacidal activity of 319-44 E345R mutant was 5 times more efficient than the wild-type antibody with an EC50 value of 0.08 nM (FIG. 5).

Other Embodiments

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. An isolated antibody that specifically binds to outer surface protein A (OspA), wherein the antibody comprises the following six CDRs:
   (a) a CDR-H1 comprising the amino acid sequence of GYSFTSYWIG (SEQ ID NO: 10);
   (b) a CDR-H2 comprising the amino acid sequence of FIYPGDSDTRYSPSFQG (SEQ ID NO: 11);
   (c) a CDR-H3 comprising the amino acid sequence of ARGILRYFDWFLDY (SEQ ID NO: 4);
   (d) a CDR-L1 comprising the amino acid sequence of RASQGISSGSA (SEQ ID NO: 12);
   (e) a CDR-L2 comprising the amino acid sequence of DVSSLES (SEQ ID NO: 7); and
   (f) a CDR-L3 comprising the amino acid sequence of QQFNSYLLT (SEQ ID NO: 8).

2. The antibody of claim 1, wherein the antibody comprises (a) a heavy chain variable domain (VH) sequence having at least 90% sequence identity to the amino acid sequence of SEQ ID NO: 13; (b) a light chain variable domain (VL) sequence having at least 90% sequence identity to the amino acid sequence of SEQ ID NO: 14; or (c) a VH sequence as in (a) and a VL sequence as in (b).

3. An isolated antibody that specifically binds to OspA, wherein the antibody comprises (a) a VH sequence comprising the amino acid sequence of SEQ ID NO: 13 and (b) a VL sequence comprising the amino acid sequence of SEQ ID NO: 14.

4. The antibody of claim 1, wherein the antibody binds to an epitope comprising amino acid residues 71-105 of OspA (SEQ ID NO: 15).

5. An isolated antibody that specifically binds to OspA, wherein the antibody comprises the following six CDRs:
   (a) a CDR-H1 comprising the amino acid sequence of GYKFSSYWIG (SEQ ID NO: 16);
   (b) a CDR-H2 comprising the amino acid sequence of IIFPGDSDKRYSPSFQG (SEQ ID NO: 17);
   (c) a CDR-H3 comprising the amino acid sequence of ARHITTHTYRGFFDF (SEQ ID NO: 5);
   (d) a CDR-L1 comprising the amino acid sequence of RASQDISSALA (SEQ ID NO: 18);
   (e) a CDR-L2 comprising the amino acid sequence of DVSSLES (SEQ ID NO: 7); and
   (f) a CDR-L3 comprising the amino acid sequence of QQFNGYPHRLT (SEQ ID NO: 9).

6. The antibody of claim 5, wherein the antibody comprises (a) a VH sequence having at least 90% sequence identity to the amino acid sequence of SEQ ID NO: 19; (b) a VL sequence having at least 90% sequence identity to the amino acid sequence of SEQ ID NO: 20; or (c) a VH sequence as in (a) and a VL sequence as in (b).

7. An isolated antibody that specifically binds to OspA, wherein the antibody comprises (a) a VH sequence comprising the amino acid sequence of SEQ ID NO: 19 and (b) a VL sequence comprising the amino acid sequence of SEQ ID NO: 20.

8. The antibody of claim 5, wherein the antibody binds to an epitope comprising amino acid residues 106-141 of OspA (SEQ ID NO: 21).

9. The antibody of claim 1, wherein the antibody binds to three or more *Borrelia* species.

10. The antibody of claim 9, wherein the three or more *Borrelia* species comprises *Borrelia burgdorferi*, *Borrelia afzelii*, and *Borrelia garinii*.

11. The antibody of claim 10, wherein the antibody binds to OspA of *Borrelia burgdorferi*, *Borrelia afzelii*, and *Borrelia garinii* with a $K_D$ of at least about 10 nM or lower.

12. The antibody of claim 9, wherein the antibody exhibits borreliacidal activity against *Borrelia* species comprising *Borrelia burgdorferi*, *Borrelia afzelii*, and *Borrelia garinii* in a borreliacidal assay.

13. An isolated antibody that specifically binds to OspA, wherein the antibody comprises the following six CDRs:
 (a) a CDR-H1 comprising the amino acid sequence of GYIFATYWIG (SEQ ID NO: 23);
 (b) a CDR-H2 comprising the amino acid sequence of IIYPNDSDTRYSPSFQG (SEQ ID NO: 24);
 (c) a CDR-H3 comprising the amino acid sequence of ARTRWYFDL (SEQ ID NO: 25);
 (d) a CDR-L1 comprising the amino acid sequence of RASQSVSSSYLA (SEQ ID NO: 26);
 (e) a CDR-L2 comprising the amino acid sequence of GASSRAT (SEQ ID NO: 27); and
 (f) a CDR-L3 comprising the amino acid sequence of QQYGSSPLT (SEQ ID NO: 28).

14. The antibody of claim 13, wherein the antibody binds to an epitope comprising amino acid residues 178-273 of OspA (SEQ ID NO: 22).

15. The antibody of claim 13, wherein the antibody comprises (a) a heavy chain variable domain (VH) sequence having at least 90% sequence identity to the amino acid sequence of SEQ ID NO: 29; (b) a light chain variable domain (VL) sequence having at least 90% sequence identity to the amino acid sequence of SEQ ID NO: 30; or (c) a VH sequence as in (a) and a VL sequence as in (b).

16. An isolated antibody that specifically binds to OspA, wherein the antibody comprises (a) a VH sequence comprising the amino acid sequence of SEQ ID NO: 29 and (b) a VL sequence comprising the amino acid sequence of SEQ ID NO: 30.

17. The antibody of claim 13, wherein the antibody binds to OspA of two or more *Borrelia* species.

18. The antibody of claim 17, wherein the two or more *Borrelia* species comprises *Borrelia burgdorferi* and *Borrelia afzelii*.

19. The antibody of claim 18, wherein the antibody binds to OspA of *Borrelia burgdorferi* and *Borrelia afzelii* with a $K_D$ of at least about 1.2 µM or lower.

20. The antibody of claim 17, wherein the antibody exhibits borreliacidal activity against *Borrelia* species comprising *Borrelia burgdorferi* and *Borrelia afzelii* in a borreliacidal assay.

21. An isolated antibody that specifically binds to OspA, wherein the antibody comprises the following six CDRs:
 (a) a CDR-H1 comprising the amino acid sequence of GFTFRNYWMD (SEQ ID NO: 32);
 (b) a CDR-H2 comprising the amino acid sequence of NIKQDGSVKYYVDSVEG (SEQ ID NO: 33);
 (c) a CDR-H3 comprising the amino acid sequence of ARDGYSGYDSVGFDI (SEQ ID NO: 34);
 (d) a CDR-L1 comprising the amino acid sequence of RASQSVSSSYLA (SEQ ID NO: 35);
 (e) a CDR-L2 comprising the amino acid sequence of DTSSRAT (SEQ ID NO: 36); and
 (f) a CDR-L3 comprising the amino acid sequence of QQYGSSPYT (SEQ ID NO: 37).

22. The antibody of claim 21, wherein the antibody comprises (a) a heavy chain variable domain (VH) sequence having at least 90% sequence identity to the amino acid sequence of SEQ ID NO: 38; (b) a light chain variable domain (VL) sequence having at least 90% sequence identity to the amino acid sequence of SEQ ID NO: 39; or (c) a VH sequence as in (a) and a VL sequence as in (b).

23. An isolated antibody that specifically binds to OspA, wherein the antibody comprises (a) a VH sequence comprising the amino acid sequence of SEQ ID NO: 38 and (b) a VL sequence comprising the amino acid sequence of SEQ ID NO: 39.

24. The antibody of claim 21, wherein the antibody binds to an epitope comprising amino acid residues 142-177 of OspA (SEQ ID NO: 31).

25. The antibody of claim 21, wherein the antibody binds to OspA of two or more *Borrelia* species.

26. The antibody of claim 25, wherein the one or more *Borrelia* species comprises *Borrelia burgdorferi*.

27. The antibody of claim 25, wherein the antibody binds to OspA of *Borrelia burgdorferi* with a $K_D$ of at least about 5 nM or lower.

28. The antibody of claim 25, wherein the antibody exhibits borreliacidal activity against *Borrelia* species comprising *Borrelia burgdorferi* in a borreliacidal assay.

29. The antibody of claim 1, wherein the antibody is monoclonal, human, humanized, or chimeric.

30. The antibody of claim 1, wherein the antibody is an antibody fragment that binds OspA.

31. The antibody of claim 30, wherein the antibody fragment is selected from the group consisting of Fab, Fab'-SH, Fv, scFv, and (Fab')$_2$ fragments.

32. The antibody of claim 1, wherein the antibody is a full-length antibody.

33. The antibody of claim 1, wherein the half-life of the antibody is 3 days.

34. A pharmaceutical composition comprising the antibody of claim 1.

35. An isolated nucleic acid encoding the antibody of claim 1.

36. A vector comprising the nucleic acid of claim 35.

37. A host cell comprising the vector of claim 36.

38. A method of producing an antibody that specifically binds to outer surface protein A (OspA), the method comprising culturing the host cell of claim 37 in a culture medium.

39. A method of treating a subject having a disorder associated with a *Borrelia* infection comprising administering to the subject a therapeutically effective amount of the antibody of claim 1, thereby treating the subject.

40. A method of treating a subject at risk of developing a disorder associated with a *Borrelia* infection comprising administering to the subject a therapeutically effective amount of the antibody of claim 1, thereby treating the subject.

41. The method of claim 39, wherein the disorder associated with a *Borrelia* infection is Lyme borreliosis (Lyme disease).

42. A method of testing a *Borrelia* vector for the presence of *Borrelia*, the method comprising contacting a sample from the *Borrelia* vector with the antibody of claim 1 and determining if binding occurs, wherein binding is indicative of the presence of a *Borrelia*.

43. A method of decreasing *Borrelia* load in a *Borrelia* vector, the method comprising providing the antibody of claim 1 to the *Borrelia* vector.

44. A method of detecting a *Borrelia* infection in a subject comprising contacting a body fluid of the subject with the antibody of claim 1 and determining if binding occurs, wherein binding is indicative of the presence of a *Borrelia* infection.

* * * * *

UNITED STATES PATENT AND TRADEMARK OFFICE
CERTIFICATE OF CORRECTION

PATENT NO. : 10,457,721 B2
APPLICATION NO. : 15/501469
DATED : October 29, 2019
INVENTOR(S) : Yang Wang et al.

Page 1 of 1

It is certified that error appears in the above-identified patent and that said Letters Patent is hereby corrected as shown below:

In the Claims

Column 72, Lines 39-40, replace "3 days" with -- $\geq$ 3 days --.

Signed and Sealed this
Seventeenth Day of December, 2019

Andrei Iancu
*Director of the United States Patent and Trademark Office*

```
                             SEQUENCE LISTING

<160> NUMBER OF SEQ ID NOS: 49

<210> SEQ ID NO 1
<211> LENGTH: 71
<212> TYPE: PRT
<213> ORGANISM: Borrelia burgdorferi

<400> SEQUENCE: 1

Asn Gly Ser Gly Val Leu Glu Gly Val Lys Ala Asp Lys Ser Lys Val
1               5                   10                  15

Lys Leu Thr Ile Ser Asp Asp Leu Gly Gln Thr Thr Leu Glu Val Phe
            20                  25                  30

Lys Glu Asp Gly Lys Thr Leu Val Ser Lys Val Thr Ser Lys Asp
        35                  40                  45

Lys Ser Ser Thr Glu Glu Lys Phe Asn Glu Lys Gly Glu Val Ser Glu
    50                  55                  60

Lys Ile Ile Thr Arg Ala Asp
65                  70

<210> SEQ ID NO 2
<211> LENGTH: 10
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Xaa is Ser or Lys
<220> FEATURE:
<221> NAME/KEY: MOD_RES
<222> LOCATION: (5)..(5)
<223> OTHER INFORMATION: Xaa is Thr or Ser

<400> SEQUENCE: 2

Gly Tyr Xaa Phe Xaa Ser Tyr Trp Ile Gly
1               5                   10

<210> SEQ ID NO 3
<211> LENGTH: 17
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Xaa is Phe or Ile
<220> FEATURE:
<221> NAME/KEY: MOD_RES
<222> LOCATION: (3)..(3)
<223> OTHER INFORMATION: Xaa is Tyr or Phe
<220> FEATURE:
<221> NAME/KEY: MOD_RES
<222> LOCATION: (9)..(9)
<223> OTHER INFORMATION: Xaa is Thr or Lys
```

```
<400> SEQUENCE: 3

Xaa Ile Xaa Pro Gly Asp Ser Asp Xaa Arg Tyr Ser Pro Ser Phe Gln
1               5                   10                  15

Gly

<210> SEQ ID NO 4
<211> LENGTH: 14
<212> TYPE: PRT
<213> ORGANISM: Homo sapiens

<400> SEQUENCE: 4

Ala Arg Gly Ile Leu Arg Tyr Phe Asp Trp Phe Leu Asp Tyr
1               5                   10

<210> SEQ ID NO 5
<211> LENGTH: 15
<212> TYPE: PRT
<213> ORGANISM: Homo sapiens

<400> SEQUENCE: 5

Ala Arg His Ile Thr Thr His Thr Tyr Arg Gly Phe Phe Asp Phe
1               5                   10                  15

<210> SEQ ID NO 6
<211> LENGTH: 11
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Xaa is Gly or Asp
<220> FEATURE:
<221> NAME/KEY: MOD_RES
<222> LOCATION: (9)..(9)
<223> OTHER INFORMATION: Xaa is Gly or Ala
<220> FEATURE:
<221> NAME/KEY: MOD_RES
<222> LOCATION: (10)..(10)
<223> OTHER INFORMATION: Xaa is Ser or Leu

<400> SEQUENCE: 6

Arg Ala Ser Gln Xaa Ile Ser Ser Xaa Xaa Ala
1               5                   10

<210> SEQ ID NO 7
<211> LENGTH: 7
<212> TYPE: PRT
<213> ORGANISM: Homo sapiens

<400> SEQUENCE: 7

Asp Val Ser Ser Leu Glu Ser
1               5

<210> SEQ ID NO 8
<211> LENGTH: 9
<212> TYPE: PRT
<213> ORGANISM: Homo sapiens

<400> SEQUENCE: 8

Gln Gln Phe Asn Ser Tyr Leu Leu Thr
1               5

<210> SEQ ID NO 9
<211> LENGTH: 11
<212> TYPE: PRT
<213> ORGANISM: Homo sapiens
```

<400> SEQUENCE: 9

Gln Gln Phe Asn Gly Tyr Pro His Arg Leu Thr
1               5                   10

<210> SEQ ID NO 10
<211> LENGTH: 10
<212> TYPE: PRT
<213> ORGANISM: Homo sapiens

<400> SEQUENCE: 10

Gly Tyr Ser Phe Thr Ser Tyr Trp Ile Gly
1               5                   10

<210> SEQ ID NO 11
<211> LENGTH: 17
<212> TYPE: PRT
<213> ORGANISM: Homo sapiens

<400> SEQUENCE: 11

Phe Ile Tyr Pro Gly Asp Ser Asp Thr Arg Tyr Ser Pro Ser Phe Gln
1               5                   10                  15
Gly

<210> SEQ ID NO 12
<211> LENGTH: 11
<212> TYPE: PRT
<213> ORGANISM: Homo sapiens

<400> SEQUENCE: 12

Arg Ala Ser Gln Gly Ile Ser Ser Gly Ser Ala
1               5                   10

<210> SEQ ID NO 13
<211> LENGTH: 121
<212> TYPE: PRT
<213> ORGANISM: Homo sapiens

<400> SEQUENCE: 13

Glu Val Gln Leu Val Gln Ser Gly Ser Glu Val Lys Lys Pro Gly Glu
1               5                   10                  15

Ser Leu Lys Ile Ser Cys Gln Val Ser Gly Tyr Ser Phe Thr Ser Tyr
                20                  25                  30

Trp Ile Gly Trp Val Arg Gln Met Pro Gly Lys Gly Leu Glu Arg Val
            35                  40                  45

Gly Phe Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Ile Leu Arg Tyr Phe Asp Trp Phe Leu Asp Tyr Trp Gly
            100                 105                 110

Gln Gly Thr Leu Val Thr Val Ser Ser
        115                 120

<210> SEQ ID NO 14
<211> LENGTH: 107
<212> TYPE: PRT
<213> ORGANISM: Homo sapiens

<400> SEQUENCE: 14

Ala Ile Gln Leu Thr Gln Ser Pro Ser Leu Ser Ala Ser Val Gly
1               5                   10                  15

Asp Arg Val Thr Ile Thr Cys Arg Ala Ser Gln Gly Ile Ser Ser
            20                  25                  30

Gly Ser Ala Trp Tyr Gln Gln Lys Pro Gly Lys Ala Pro Lys Leu
        35                  40                  45

Leu Ile Tyr Asp Val Ser Ser Leu Glu Ser Gly Val Pro Ser Arg
        50                  55                  60

Phe Ser Gly Ser Gly Ser Gly Thr Glu Phe Thr Leu Thr Ile Ser
65                  70                  75

Ser Leu Gln Pro Glu Asp Phe Ala Thr Tyr Tyr Cys Gln Gln Phe
                80                  85                  90

Asn Ser Tyr Leu Leu Thr Phe Gly Gly Gly Thr Lys Val Glu Ile
                95                  100                 105

Lys

<210> SEQ ID NO 15
<211> LENGTH: 35
<212> TYPE: PRT
<213> ORGANISM: Borrelia burgdorferi

<400> SEQUENCE: 15

Asn Gly Ser Gly Val Leu Glu Gly Val Lys Ala Asp Lys Ser Lys
1               5                   10                  15

Val Lys Leu Thr Ile Ser Asp Asp Leu Gly Gln Thr Thr Leu Glu
                20                  25                  30

Val Phe Lys Glu Asp
                35

<210> SEQ ID NO 16
<211> LENGTH: 10
<212> TYPE: PRT
<213> ORGANISM: Homo sapiens

<400> SEQUENCE: 16

Gly Tyr Lys Phe Ser Ser Tyr Trp Ile Gly
1               5                   10

<210> SEQ ID NO 17
<211> LENGTH: 17
<212> TYPE: PRT
<213> ORGANISM: Homo sapiens

<400> SEQUENCE: 17

Ile Ile Phe Pro Gly Asp Ser Asp Lys Arg Tyr Ser Pro Ser Phe
1               5                   10                  15

Gln Gly

<210> SEQ ID NO 18
<211> LENGTH: 11
<212> TYPE: PRT
<213> ORGANISM: Homo sapiens

<400> SEQUENCE: 18

Arg Ala Ser Gln Asp Ile Ser Ser Ala Leu Ala
1               5                   10

<210> SEQ ID NO 19
<211> LENGTH: 122
<212> TYPE: PRT

<213> ORGANISM: Homo sapiens

<400> SEQUENCE: 19

Glu Val Gln Leu Val Gln Ser Gly Glu Val Lys Lys Pro Gly Glu
1               5                   10                  15

Ser Leu Lys Ile Ser Cys Lys Gly Ser Gly Tyr Lys Phe Ser Ser Tyr
            20                  25                  30

Trp Ile Gly Trp Val Arg Gln Met Pro Gly Lys Gly Leu Glu Trp Met
        35                  40                  45

Gly Ile Ile Phe Pro Gly Asp Ser Asp Lys Arg Tyr Ser Pro Ser Phe
    50                  55                  60

Gln Gly Gln Val Thr Ile Ser Ala Asp Lys Ser Ile Ser Thr Val Tyr
65                  70                  75                  80

Leu Gln Trp Ser Ser Leu Lys Ala Ser Asp Thr Ala Met Tyr Tyr Cys
                85                  90                  95

Ala Arg His Ile Thr Thr His Thr Tyr Arg Gly Phe Phe Asp Phe Trp
            100                 105                 110

Gly Gln Gly Thr Leu Val Thr Val Ser Ser
        115                 120

<210> SEQ ID NO 20
<211> LENGTH: 109
<212> TYPE: PRT
<213> ORGANISM: Homo sapiens

<400> SEQUENCE: 20

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Ala
            20                  25                  30

Leu Ala Trp Tyr Gln Gln Lys Pro Gly Lys Ala Pro Lys Leu Leu Ile
        35                  40                  45

Tyr Asp Val Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Gly Tyr Pro His
                85                  90                  95

Arg Leu Thr Phe Gly Gly Gly Thr Lys Val Glu Ile Lys
            100                 105

<210> SEQ ID NO 21
<211> LENGTH: 36
<212> TYPE: PRT
<213> ORGANISM: Borrelia burgdorferi

<400> SEQUENCE: 21

Gly Lys Thr Leu Val Ser Lys Lys Val Thr Ser Lys Asp Lys Ser Ser
1               5                   10                  15

Thr Glu Glu Lys Phe Asn Glu Lys Gly Glu Val Ser Glu Lys Ile Ile
            20                  25                  30

Thr Arg Ala Asp
        35

<210> SEQ ID NO 22
<211> LENGTH: 96
<212> TYPE: PRT
<213> ORGANISM: Borrelia burgdorferi

<400> SEQUENCE: 22

Leu Val Val Lys Glu Gly Thr Val Thr Leu Ser Lys Asn Ile Ser Lys
1               5                   10                  15

Ser Gly Glu Val Ser Val Glu Leu Asn Asp Thr Asp Ser Ser Ala Ala
            20                  25                  30

Thr Lys Lys Thr Ala Ala Trp Asn Ser Gly Thr Ser Thr Leu Thr Ile
        35                  40                  45

Thr Val Asn Ser Lys Lys Thr Lys Asp Leu Val Phe Thr Lys Glu Asn
    50                  55                  60

Thr Ile Thr Val Gln Gln Tyr Asp Ser Asn Gly Thr Lys Leu Glu Gly
65                  70                  75                  80

Ser Ala Val Glu Ile Thr Lys Leu Asp Glu Ile Lys Asn Ala Leu Lys
                85                  90                  95

<210> SEQ ID NO 23
<211> LENGTH: 10
<212> TYPE: PRT
<213> ORGANISM: Homo sapiens

<400> SEQUENCE: 23

Gly Tyr Ile Phe Ala Thr Tyr Trp Ile Gly
1               5                   10

<210> SEQ ID NO 24
<211> LENGTH: 17
<212> TYPE: PRT
<213> ORGANISM: Homo sapiens

<400> SEQUENCE: 24

Ile Ile Tyr Pro Asn Asp Ser Asp Thr Arg Tyr Ser Pro Ser Phe Gln
1               5                   10                  15

Gly

<210> SEQ ID NO 25
<211> LENGTH: 9
<212> TYPE: PRT
<213> ORGANISM: Homo sapiens

<400> SEQUENCE: 25

Ala Arg Thr Arg Trp Tyr Phe Asp Leu
1               5

<210> SEQ ID NO 26
<211> LENGTH: 12
<212> TYPE: PRT
<213> ORGANISM: Homo sapiens

<400> SEQUENCE: 26

Arg Ala Ser Gln Ser Val Ser Ser Ser Tyr Leu Ala
1               5                   10

<210> SEQ ID NO 27
<211> LENGTH: 7
<212> TYPE: PRT
<213> ORGANISM: Homo sapiens

<400> SEQUENCE: 27

Gly Ala Ser Ser Arg Ala Thr
1               5

<210> SEQ ID NO 28
<211> LENGTH: 9
<212> TYPE: PRT
<213> ORGANISM: Homo sapiens

<400> SEQUENCE: 28

Gln Gln Tyr Gly Ser Ser Pro Leu Thr
1               5

<210> SEQ ID NO 29
<211> LENGTH: 116
<212> TYPE: PRT
<213> ORGANISM: Homo sapiens

<400> SEQUENCE: 29

Glu Met Gln Leu Val Gln Ser Gly Ala Glu Val Lys Lys Pro Gly Glu
1               5                   10                  15

Ser Leu Lys Ile Ser Cys Lys Gly Ser Gly Tyr Ile Phe Ala Thr Tyr
            20                  25                  30

Trp Ile Gly Trp Val Arg Gln Met Pro Gly Lys Gly Leu Glu Trp Met
        35                  40                  45

Gly Ile Ile Tyr Pro Asn Asp Ser Asp Thr Arg Tyr Ser Pro Ser Phe
    50                  55                  60

Gln Gly Gln Val Thr Ile Ser Ala Asp Lys Ser Ile Asn Thr Ala Tyr
65                  70                  75                  80

Leu Gln Trp Ser Ser Leu Lys Ala Ser Asp Thr Ala Met Tyr Tyr Cys
                85                  90                  95

Ala Arg Thr Arg Trp Tyr Phe Asp Leu Trp Gly Arg Gly Thr Leu Val
            100                 105                 110

Thr Val Ser Ser
        115

<210> SEQ ID NO 30
<211> LENGTH: 108
<212> TYPE: PRT
<213> ORGANISM: Homo sapiens

<400> SEQUENCE: 30

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys
            100                 105

<210> SEQ ID NO 31
<211> LENGTH: 36
<212> TYPE: PRT
<213> ORGANISM: Borrelia burgdorferi

<400> SEQUENCE: 31

Gly Thr Arg Leu Glu Tyr Thr Gly Ile Lys Ser Asp Gly Ser Gly Lys
1               5                   10                  15

Ala Lys Glu Val Leu Lys Gly Tyr Val Leu Glu Gly Leu Thr Ala
            20                  25                  30

Glu Lys Thr Thr
        35

<210> SEQ ID NO 32
<211> LENGTH: 10
<212> TYPE: PRT
<213> ORGANISM: Homo sapiens

<400> SEQUENCE: 32

Gly Phe Thr Phe Arg Asn Tyr Trp Met Asp
1               5                   10

<210> SEQ ID NO 33
<211> LENGTH: 17
<212> TYPE: PRT
<213> ORGANISM: Homo sapiens

<400> SEQUENCE: 33

Asn Ile Lys Gln Asp Gly Ser Val Lys Tyr Tyr Val Asp Ser Val Glu
1               5                   10                  15

Gly

<210> SEQ ID NO 34
<211> LENGTH: 15
<212> TYPE: PRT
<213> ORGANISM: Homo sapiens

<400> SEQUENCE: 34

Ala Arg Asp Gly Tyr Ser Gly Tyr Asp Ser Val Gly Phe Asp Ile
1               5                   10                  15

<210> SEQ ID NO 35
<211> LENGTH: 12
<212> TYPE: PRT
<213> ORGANISM: Homo sapiens

<400> SEQUENCE: 35

Arg Ala Ser Gln Ser Val Ser Ser Ser Tyr Leu Ala
1               5                   10

<210> SEQ ID NO 36
<211> LENGTH: 7
<212> TYPE: PRT
<213> ORGANISM: Homo sapiens

<400> SEQUENCE: 36

Asp Thr Ser Ser Arg Ala Thr
1               5

<210> SEQ ID NO 37
<211> LENGTH: 9
<212> TYPE: PRT
<213> ORGANISM: Homo sapiens

<400> SEQUENCE: 37

Gln Gln Tyr Gly Ser Ser Pro Tyr Thr
1               5

<210> SEQ ID NO 38

```
<211> LENGTH: 122
<212> TYPE: PRT
<213> ORGANISM: Homo sapiens

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Asn Tyr
            20                  25                  30

Trp Met Asp Trp Val Arg Gln Ala Pro Gly Lys Gly Leu Glu Trp Val
        35                  40                  45

Ala Asn Ile Lys Gln Asp Gly Ser Val Lys Tyr Tyr Val Asp Ser Val
    50                  55                  60

Glu Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Gly Tyr Ser Gly Tyr Asp Ser Val Gly Phe Asp Ile Trp
            100                 105                 110

Gly Gln Gly Thr Met Val Thr Val Ser Ser
        115                 120

<210> SEQ ID NO 39
<211> LENGTH: 108
<212> TYPE: PRT
<213> ORGANISM: Homo sapiens

<400> SEQUENCE: 39

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Ser Asp Thr Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Tyr Thr Phe Gly Gln Gly Thr Lys Leu Glu Ile Lys
            100                 105

<210> SEQ ID NO 40
<211> LENGTH: 273
<212> TYPE: PRT
<213> ORGANISM: Borrelia burgdorferi

<400> SEQUENCE: 40

Met Lys Lys Tyr Leu Leu Gly

Gly Thr Ser Asp Lys Asn Asn Gly Ser Gly Val Leu Glu Gly Val Lys
65                  70                  75                  80

Ala Asp Lys Ser Lys Val Lys Leu Thr Ile Ser Asp Asp Leu Gly Gln
                85                  90                  95

Thr Thr Leu Glu Val Phe Lys Glu Asp Gly Lys Thr Leu Val Ser Lys
            100                 105                 110

Lys Val Thr Ser Lys Asp Lys Ser Ser Thr Glu Glu Lys Phe Asn Glu
        115                 120                 125

Lys Gly Glu Val Ser Glu Lys Ile Ile Thr Arg Ala Asp Gly Thr Arg
    130                 135                 140

Leu Glu Tyr Thr Gly Ile Lys Ser Asp Gly Ser Gly Lys Ala Lys Glu
145                 150                 155                 160

Val Leu Lys Gly Tyr Val Leu Glu Gly Thr Leu Thr Ala Glu Lys Thr
                165                 170                 175

Thr Leu Val Val Lys Glu Gly Thr Val Thr Leu Ser Lys Asn Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ser Gly Thr Ser Thr Leu Thr
    210                 215                 220

Ile Thr Val Asn Ser Lys Lys Thr Lys Asp Leu Val Phe Thr Lys Glu
225                 230                 235                 240

Asn Thr Ile Thr Val Gln Gln Tyr Asp Ser Asn Gly Thr Lys Leu Glu
                245                 250                 255

Gly Ser Ala Val Glu Ile Thr Lys Leu Asp Glu Ile Lys Asn Ala Leu
            260                 265                 270

Lys

<210> SEQ ID NO 41
<211> LENGTH: 273
<212> TYPE: PRT
<213> ORGANISM: Borrelia afzelii

<400> SEQUENCE: 41

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Ala Ser Val
                20                  25                  30

Asp Leu Pro Gly Glu Met Lys Val Leu Val Ser Lys Glu Lys Asp Lys
            35                  40                  45

Asp Gly Lys Tyr Ser Leu Lys Ala Thr Val Asp Lys Ile Glu Leu Lys
        50                  55                  60

Gly Thr Ser Asp Lys Asp Asn Gly Ser Gly Val Leu Glu Gly Thr Lys
65                  70                  75                  80

Asp Asp Lys Ser Lys Ala Lys Leu Thr Ile Ala Asp Asp Leu Ser Lys
                85                  90                  95

Thr Thr Phe Glu Leu Phe Lys Glu Asp Gly Lys Thr Leu Val Ser Arg
            100                 105                 110

Lys Val Ser Ser Lys Asp Lys Thr Ser Thr Asp Glu Met Phe Asn Glu
        115                 120                 125

Lys Gly Glu Leu Ser Ala Lys Thr Met Thr Arg Glu Asn Gly Thr Lys
    130                 135                 140

Leu Glu Tyr Thr Glu Met Lys Ser Asp Gly Thr Gly Lys Ala Lys Glu
145                 150                 155                 160

Val Leu Lys Asn Phe Thr Leu Glu Gly Lys Val Ala Asn Asp Lys Val
            165                 170                 175

Thr Leu Glu Val Lys Glu Gly Thr Val Thr Leu Ser Lys Glu Ile Ala
        180                 185                 190

Lys Ser Gly Glu Val Thr Val Ala Leu Asn Asp Thr Asn Thr Thr Gln
        195                 200                 205

Ala Thr Lys Lys Thr Gly Ala Trp Asp Ser Lys Thr Ser Thr Leu Thr
        210                 215                 220

Ile Ser Val Asn Ser Lys Thr Thr Gln Leu Val Phe Thr Lys Gln
225                 230                 235                 240

Asp Thr Ile Thr Val Gln Lys Tyr Asp Ser Ala Gly Thr Asn Leu Glu
        245                 250                 255

Gly Thr Ala Val Glu Ile Lys Thr Leu Asp Glu Leu Lys Asn Ala Leu
        260                 265                 270

Lys

<210> SEQ ID NO 42
<211> LENGTH: 273
<212> TYPE: PRT
<213> ORGANISM: Borrelia garinii

<400> SEQUENCE: 42

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
                20                  25                  30

Asp Leu Pro Gly Glu Met Lys Val Leu Val Ser Lys Glu Lys Asp Lys
            35                  40                  45

Asp Gly Lys Tyr Ser Leu Met Ala Thr Val Asp Lys Leu Glu Leu Lys
        50                  55                  60

Gly Thr Ser Asp Lys Ser Asn Gly Ser Gly Thr Leu Glu Gly Glu Lys
65                  70                  75                  80

Ser Asp Lys Ser Lys Ala Lys Leu Thr Ile Ser Glu Asp Leu Ser Lys
                85                  90                  95

Thr Thr Phe Glu Ile Phe Lys Glu Asp Gly Lys Thr Leu Val Ser Lys
            100                 105                 110

Lys Val Asn Ser Lys Asp Lys Ser Ser Ile Glu Glu Lys Phe Asn Ala
        115                 120                 125

Lys Gly Glu Leu Ser Glu Lys Thr Ile Leu Arg Ala Asn Gly Thr Arg
    130                 135                 140

Leu Glu Tyr Thr Glu Ile Lys Ser Asp Gly Thr Gly Lys Ala Lys Glu
145                 150                 155                 160

Val Leu Lys Asp Phe Ala Leu Glu Gly Thr Leu Ala Ala Asp Lys Thr
                165                 170                 175

Thr Leu Lys Val Thr Glu Gly Thr Val Val Leu Ser Lys His Ile Pro
            180                 185                 190

Asn Ser Gly Glu Ile Thr Val Glu Leu Asn Asp Ser Asn Ser Thr Gln
        195                 200                 205

Ala Thr Lys Lys Thr Gly Lys Trp Asp Ser Asn Thr Ser Thr Leu Thr
    210                 215                 220

Ile Ser Val Asn Ser Lys Lys Thr Lys Asn Ile Val Phe Thr Lys Glu
225                 230                 235                 240

Asp Thr Ile Thr Val Gln Lys Tyr Asp Ser Ala Gly Thr Asn Leu Glu
                245                 250                 255

Gly Asn Ala Val Glu Ile Lys Thr Leu Asp Glu Leu Lys Asn Ala Leu
            260                 265                 270

Lys

<210> SEQ ID NO 43
<211> LENGTH: 256
<212> TYPE: PRT
<213> ORGANISM: Borrelia burgdorferi

<400> SEQUENCE: 43

Lys Gln Asn Val Ser Ser Leu Asp Glu Lys Asn Ser Val Ser Val Asp
1               5                   10                  15

Leu Pro Gly Glu Met Lys Val Leu Val Ser Lys Glu Lys Asn Lys Asp
            20                  25                  30

Gly Lys Tyr Asp Leu Ile Ala Thr Val Asp Lys Leu Glu Leu Lys Gly
        35                  40                  45

Thr Ser Asp Lys Asn Asn Gly Ser Gly Val Leu Glu Gly Val Lys Ala
    50                  55                  60

Asp Lys Ser Lys Val Lys Leu Thr Ile Ser Asp Asp Leu Gly Gln Thr
65                  70                  75                  80

Thr Leu Glu Val Phe Lys Glu Asp Gly Lys Thr Leu Val Ser Lys Lys
                85                  90                  95

Val Thr Ser Lys Asp Lys Ser Ser Thr Glu Glu Lys Phe Asn Glu Lys
            100                 105                 110

Gly Glu Val Ser Glu Lys Ile Ile Thr Arg Ala Asp Gly Thr Arg Leu
        115                 120                 125

Glu Tyr Thr Gly Ile Lys Ser Asp Gly Ser Gly Lys Ala Lys Glu Val
    130                 135                 140

Leu Lys Gly Tyr Val Leu Glu Gly Thr Leu Thr Ala Glu Lys Thr Thr
145                 150                 155                 160

Leu Val Val Lys Glu Gly Thr Val Thr Leu Ser Lys Asn Ile Ser Lys
                165                 170                 175

Ser Gly Glu Val Ser Val Glu Leu Asn Asp Thr Asp Ser Ser Ala Ala
            180                 185                 190

Thr Lys Lys Thr Ala Ala Trp Asn Ser Gly Thr Ser Thr Leu Thr Ile
        195                 200                 205

Thr Val Asn Ser Lys Lys Thr Lys Asp Leu Val Phe Thr Lys Glu Asn
    210                 215                 220

Thr Ile Thr Val Gln Gln Tyr Asp Ser Asn Gly Thr Lys Leu Glu Gly
225                 230                 235                 240

Ser Ala Val Glu Ile Thr Lys Leu Asp Glu Ile Lys Asn Ala Leu Lys
                245                 250                 255

<210> SEQ ID NO 44
<211> LENGTH: 124
<212> TYPE: PRT
<213> ORGANISM: Borrelia burgdorferi

<400> SEQUENCE: 44

Lys Gln Asn Val Ser Ser Leu Asp Glu Lys Asn Ser Val Ser Val Asp
1               5                   10                  15

Leu Pro Gly Glu Met Lys Val Leu Val Ser Lys Glu Lys Asn Lys Asp
            20                  25                  30

Gly Lys Tyr Asp Leu Ile Ala Thr Val Asp Lys Leu Glu Leu Lys Gly
        35                  40                  45

Thr Ser Asp Lys Asn Asn Gly Ser Gly Val Leu Glu Gly Val Lys Ala

```
            50                  55                  60
Asp Lys Ser Lys Val Lys Leu Thr Ile Ser Asp Asp Leu Gly Gln Thr
 65                  70                  75                  80

Thr Leu Glu Val Phe Lys Glu Asp Gly Lys Thr Leu Val Ser Lys Lys
                 85                  90                  95

Val Thr Ser Lys Asp Lys Ser Ser Thr Glu Glu Lys Phe Asn Glu Lys
                100                 105                 110

Gly Glu Val Ser Glu Lys Ile Ile Thr Arg Ala Asp
            115                 120
```

<210> SEQ ID NO 45
<211> LENGTH: 160
<212> TYPE: PRT
<213> ORGANISM: Borrelia burgdorferi

<400> SEQUENCE: 45

```
Lys Gln Asn Val Ser Ser Leu Asp Glu Lys Asn Ser Val Ser Val Asp
 1               5                  10                  15

Leu Pro Gly Glu Met Lys Val Leu Val Ser Lys Glu Lys Asn Lys Asp
                20                  25                  30

Gly Lys Tyr Asp Leu Ile Ala Thr Val Asp Lys Leu Glu Leu Lys Gly
            35                  40                  45

Thr Ser Asp Lys Asn Asn Gly Ser Gly Val Leu Glu Gly Val Lys Ala
 50                  55                  60

Asp Lys Ser Lys Val Lys Leu Thr Ile Ser Asp Asp Leu Gly Gln Thr
 65                  70                  75                  80

Thr Leu Glu Val Phe Lys Glu Asp Gly Lys Thr Leu Val Ser Lys Lys
                 85                  90                  95

Val Thr Ser Lys Asp Lys Ser Ser Thr Glu Glu Lys Phe Asn Glu Lys
                100                 105                 110

Gly Glu Val Ser Glu Lys Ile Ile Thr Arg Ala Asp Gly Thr Arg Leu
            115                 120                 125

Glu Tyr Thr Gly Ile Lys Ser Asp Gly Ser Gly Lys Ala Lys Glu Val
            130                 135                 140

Leu Lys Gly Tyr Val Leu Glu Gly Thr Leu Thr Ala Glu Lys Thr Thr
145                 150                 155                 160
```

<210> SEQ ID NO 46
<211> LENGTH: 203
<212> TYPE: PRT
<213> ORGANISM: Borrelia burgdorferi

<400> SEQUENCE: 46

```
Asn Gly Ser Gly Val Leu Glu Gly Val Lys Ala Asp Lys Ser Lys Val
 1               5                  10                  15

Lys Leu Thr Ile Ser Asp Asp Leu Gly Gln Thr Thr Leu Glu Val Phe
                20                  25                  30

Lys Glu Asp Gly Lys Thr Leu Val Ser Lys Lys Val Thr Ser Lys Asp
            35                  40                  45

Lys Ser Ser Thr Glu Glu Lys Phe Asn Glu Lys Gly Glu Val Ser Glu
 50                  55                  60

Lys Ile Ile Thr Arg Ala Asp Gly Thr Arg Leu Glu Tyr Thr Gly Ile
 65                  70                  75                  80

Lys Ser Asp Gly Ser Gly Lys Ala Lys Glu Val Leu Lys Gly Tyr Val
                 85                  90                  95

Leu Glu Gly Thr Leu Thr Ala Glu Lys Thr Thr Leu Val Val Lys Glu
```

```
                100             105             110
Gly Thr Val Thr Leu Ser Lys Asn Ile Ser Lys Ser Gly Glu Val Ser
            115                 120                 125

Val Glu Leu Asn Asp Thr Asp Ser Ser Ala Ala Thr Lys Lys Thr Ala
        130                 135                 140

Ala Trp Asn Ser Gly Thr Ser Thr Leu Thr Ile Thr Val Asn Ser Lys
145                 150                 155                 160

Lys Thr Lys Asp Leu Val Phe Thr Lys Glu Asn Thr Ile Thr Val Gln
                165                 170                 175

Gln Tyr Asp Ser Asn Gly Thr Lys Leu Glu Gly Ser Ala Val Glu Ile
            180                 185                 190

Thr Lys Leu Asp Glu Ile Lys Asn Ala Leu Lys
            195                 200

<210> SEQ ID NO 47
<211> LENGTH: 168
<212> TYPE: PRT
<213> ORGANISM: Borrelia burgdorferi

<400> SEQUENCE: 47

Gly Lys Thr Leu Val Ser Lys Lys Val Thr Ser Lys Asp Lys Ser Ser
1               5                   10                  15

Thr Glu Glu Lys Phe Asn Glu Lys Gly Glu Val Ser Glu Lys Ile Ile
                20                  25                  30

Thr Arg Ala Asp Gly Thr Arg Leu Glu Tyr Thr Gly Ile Lys Ser Asp
            35                  40                  45

Gly Ser Gly Lys Ala Lys Glu Val Leu Lys Gly Tyr Val Leu Glu Gly
        50                  55                  60

Thr Leu Thr Ala Glu Lys Thr Thr Leu Val Val Lys Glu Gly Thr Val
65                  70                  75                  80

Thr Leu Ser Lys Asn Ile Ser Lys Ser Gly Glu Val Ser Val Glu Leu
                85                  90                  95

Asn Asp Thr Asp Ser Ser Ala Ala Thr Lys Lys Thr Ala Ala Trp Asn
                100                 105                 110

Ser Gly Thr Ser Thr Leu Thr Ile Thr Val Asn Ser Lys Lys Thr Lys
            115                 120                 125

Asp Leu Val Phe Thr Lys Glu Asn Thr Ile Thr Val Gln Gln Tyr Asp
        130                 135                 140

Ser Asn Gly Thr Lys Leu Glu Gly Ser Ala Val Glu Ile Thr Lys Leu
145                 150                 155                 160

Asp Glu Ile Lys Asn Ala Leu Lys
                165

<210> SEQ ID NO 48
<211> LENGTH: 132
<212> TYPE: PRT
<213> ORGANISM: Borrelia burgdorferi

<400> SEQUENCE: 48

Gly Thr Arg Leu Glu Tyr Thr Gly Ile Lys Ser Asp Gly Ser Gly Lys
1               5                   10                  15

Ala Lys Glu Val Leu Lys Gly Tyr Val Leu Glu Gly Thr Leu Thr Ala
                20                  25                  30

Glu Lys Thr Thr Leu Val Val Lys Glu Gly Thr Val Thr Leu Ser Lys
            35                  40                  45

Asn Ile Ser Lys Ser Gly Glu Val Ser Val Glu Leu Asn Asp Thr Asp
```

```
                   50                  55                  60
Ser Ser Ala Ala Thr Lys Lys Thr Ala Ala Trp Asn Ser Gly Thr Ser
65                  70                  75                  80

Thr Leu Thr Ile Thr Val Asn Ser Lys Lys Thr Lys Asp Leu Val Phe
                85                  90                  95

Thr Lys Glu Asn Thr Ile Thr Val Gln Gln Tyr Asp Ser Asn Gly Thr
            100                 105                 110

Lys Leu Glu Gly Ser Ala Val Glu Ile Thr Lys Leu Asp Glu Ile Lys
        115                 120                 125

Asn Ala Leu Lys
    130

<210> SEQ ID NO 49
<211> LENGTH: 96
<212> TYPE: PRT
<213> ORGANISM: Borrelia burgdorferi

<400> SEQUENCE: 49

Leu Val Val Lys Glu Gly Thr Val Thr Leu Ser Lys Asn Ile Ser Lys
1               5                   10                  15

Ser Gly Glu Val Ser Val Glu Leu Asn Asp Thr Asp Ser Ser Ala Ala
            20                  25                  30

Thr Lys Lys Thr Ala Ala Trp Asn Ser Gly Thr Ser Thr Leu Thr Ile
        35                  40                  45

Thr Val Asn Ser Lys Lys Thr Lys Asp Leu Val Phe Thr Lys Glu Asn
    50                  55                  60

Thr Ile Thr Val Gln Gln Tyr Asp Ser Asn Gly Thr Lys Leu Glu Gly
65                  70                  75                  80

Ser Ala Val Glu Ile Thr Lys Leu Asp Glu Ile Lys Asn Ala Leu Lys
                85                  90                  95
```